(12) United States Patent
Bradway et al.

(10) Patent No.: US 12,740,879 B2
(45) Date of Patent: Sep. 22, 2026

(54) MODULAR HANDLE COMPRISING A TRIGGER WIRE ACTUATION MECHANISM FOR A PROSTHESIS DELIVERY DEVICE

(71) Applicant: Cook Medical Technologies LLC, Bloomington, IN (US)

(72) Inventors: Ryan C. Bradway, Temecula, CA (US); Charles L. Baxter, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 18/748,926

(22) Filed: Jun. 20, 2024

(65) Prior Publication Data

US 2024/0341985 A1 Oct. 17, 2024

Related U.S. Application Data

(63) Continuation of application No. 18/073,014, filed on Dec. 1, 2022, now Pat. No. 12,029,668, which is a
(Continued)

(51) Int. Cl.
*A61F 2/966* (2013.01)
*A61F 2/95* (2013.01)
(Continued)

(52) U.S. Cl.
CPC ............ *A61F 2/9517* (2020.05); *A61F 2/954* (2013.01); *A61F 2/958* (2013.01); *A61F 2/966* (2013.01);
(Continued)

(58) Field of Classification Search
CPC ........ A61F 2/9517; A61F 2/954; A61F 2/958; A61F 2/966; A61F 2/97; A61F 2/07;
(Continued)

(56) References Cited

U.S. PATENT DOCUMENTS 5,776,142 A 7/1998 Gunderson
5,906,619 A 5/1999 Olson
(Continued)

FOREIGN PATENT DOCUMENTS

EP 0696447 A2 2/1996
EP 0873733 A1 10/1998
(Continued)

OTHER PUBLICATIONS

Examination Report for EP Application No. 16275123, dated Oct. 20, 2021, 5 pages.
(Continued)

*Primary Examiner* — Jing Rui Ou

(74) *Attorney, Agent, or Firm* — MacMillan, Sobanski & Todd, LLC

(57) ABSTRACT

A handle assembly for a prosthesis delivery device is disclosed. The handle assembly includes a main handle, a rotatable handle, a retractable sheath operatively coupled to the rotatable handle, at least one rotatable ring having a rotatable inner surface, the at least one rotatable ring coupled to a distal end of at least one trigger wire, and the at least one trigger wire having a proximal end configured to releasably engage a prosthesis. Rotation of the rotatable handle is configured to retract the sheath in a distal direction and rotation of the at least one rotatable ring is configured to wind at least a portion of the trigger wire onto the rotatable inner surface and withdraw the at least one trigger wire in the distal direction.

21 Claims, 14 Drawing Sheets

Related U.S. Application Data continuation of application No. 16/419,282, filed on May 22, 2019, now abandoned, which is a continuation of application No. 15/244,501, filed on Aug. 23, 2016, now Pat. No. 10,335,301.

(60) Provisional application No. 62/212,767, filed on Sep. 1, 2015.

(51) Int. Cl.
*A61F 2/954* (2013.01)
*A61F 2/958* (2013.01)
*A61F 2/97* (2013.01)
*A61F 2/07* (2013.01)

(52) U.S. Cl.
CPC *A61F 2/97* (2013.01); *A61F 2/07* (2013.01); *A61F 2002/9511* (2013.01); *A61F 2/9522* (2020.05); *A61F 2002/9665* (2013.01); *A61F 2220/005* (2013.01); *A61F 2220/0058* (2013.01); *A61F 2250/006* (2013.01); *A61F 2250/0069* (2013.01); *A61F 2250/0098* (2013.01); *A61F 2310/00017* (2013.01); *A61F 2310/00023* (2013.01)

(58) Field of Classification Search
CPC ............ A61F 2/9522; A61F 2002/9511; A61F 2002/9665; A61F 2220/005; A61F 2220/0058; A61F 2250/006; A61F 2250/0069; A61F 2250/0098; A61F 2310/00017; A61F 2310/00023
See application file for complete search history.

(56) References Cited

U.S. PATENT DOCUMENTS 6,203,550 B1 3/2001 Olson
6,866,666 B1 3/2005 Sinnott
6,911,039 B2 6/2005 Shiu
7,105,016 B2 9/2006 Shiu et al.
7,419,501 B2 9/2008 Shiu et al.
8,518,098 B2 8/2013 Roeder
8,968,380 B2 3/2015 Nimgaard
9,603,696 B2 3/2017 Hartley
9,629,737 B2 4/2017 Bowe
9,717,614 B2 8/2017 Farag Eells
2003/0060772 A1 3/2003 Swenson
2003/0191516 A1 10/2003 Weldon et al.
2003/0225446 A1 12/2003 Hartley
2003/0233140 A1 12/2003 Hartley
2004/0098079 A1 5/2004 Hartley
2004/0106974 A1 6/2004 Greenberg
2004/0127912 A1 7/2004 Rabkin
2004/0138734 A1 7/2004 Chobotov et al.
2004/0230287 A1 11/2004 Hartley
2005/0027305 A1 2/2005 Shiu et al.
2005/0049674 A1 3/2005 Berra
2005/0080476 A1 4/2005 Gunderson
2005/0228475 A1 10/2005 Keeble
2006/0004433 A1 1/2006 Greenberg
2006/0100640 A1 5/2006 Bolduc
2006/0236742 A1 10/2006 Monahan
2007/0250069 A1 10/2007 Carlson et al.
2007/0255390 A1 11/2007 Ducke
2009/0312748 A1 12/2009 Johnson
2009/0312829 A1 12/2009 Aoba
2010/0094393 A1 4/2010 Cordeiro et al.
2010/0198328 A1 8/2010 Hartley
2010/0274340 A1 10/2010 Hartley
2011/0224774 A1 9/2011 Silveira et al.
2011/0270371 A1 11/2011 Argentine
2011/0270372 A1 11/2011 Argentine
2011/0288558 A1 11/2011 Nimgaard
2011/0307048 A1* 12/2011 Ivancev .................. A61F 2/954 623/1.11
2011/0307049 A1 12/2011 Kao
2012/0041547 A1 2/2012 Duffy et al.
2012/0053574 A1 3/2012 Murray, III et al.
2012/0221091 A1 8/2012 Hartly
2012/0323302 A1 12/2012 Brinser
2013/0110041 A1 5/2013 Farag
2013/0131774 A1 5/2013 Nabulsi
2013/0144276 A1 6/2013 Crisostomo
2013/0190859 A1 7/2013 Hillukka
2013/0261725 A1* 10/2013 Hendriksen ............... A61F 2/95 623/1.11
2013/0274859 A1 10/2013 Argentine
2013/0289646 A1 10/2013 Libbus et al.
2013/0289691 A1 10/2013 Argentine et al.
2013/0289692 A1 10/2013 Argentine et al.
2013/0289693 A1 10/2013 Maggard et al.
2013/0289696 A1 10/2013 Maggard et al.
2014/0114392 A1 4/2014 McDonald
2014/0121755 A1 5/2014 Farag
2014/0180386 A1 6/2014 Huser
2015/0148894 A1 5/2015 Damm et al.
2015/0230955 A1 8/2015 Farag
2016/0074625 A1 3/2016 Furnish
2016/0106564 A1 4/2016 Roeder et al.
2016/0120677 A1 5/2016 Heanue
2016/0256301 A1 9/2016 Roeder et al.
2016/0338864 A1 11/2016 Vad et al.
2016/0376851 A1 12/2016 Morrow

FOREIGN PATENT DOCUMENTS

EP 0990426 A1 4/2000
EP 2522315 A1 11/2012
EP 2617388 A2 7/2013
EP 2907485 A1 8/2015
GB 2474252 A 4/2011
GB 2491478 A 12/2012
WO WO 98/53761 A1 12/1998
WO WO 00/61035 A1 10/2000
WO WO 03/068302 A2 8/2003
WO WO 03/101518 12/2003
WO WO 2004/103434 A1 12/2004
WO WO 2006/037086 A1 4/2006
WO WO 2008/066923 A1 6/2008
WO WO 2010/022138 A2 2/2010
WO WO 2010/044851 A1 4/2010
WO WO 2010/098804 A1 9/2010
WO WO 2011/049808 A1 4/2011
WO WO 2011/059707 A1 5/2011
WO WO 2011/133272 A1 10/2011
WO WO 2012/032147 A2 3/2012

OTHER PUBLICATIONS

Extended European Search Report for EP Application No. 16275123, dated Oct. 27, 2016, 7 pages.
Extended European Search Report for EP Application No. 16275124, dated Oct. 27, 2016, 5 pages.
Partial European Search Report for EP Application No. 16275125, dated Oct. 27, 2016, 6 pages.
Extended European Search Report for EP Application No. 16275125, dated Nov. 28, 2016, 11 pages.
Examination Report of EP Application No. 16275125, dated Feb. 19, 2019, 4 pages.
Extended European Search Report for EP Application No. 16275126, dated Oct. 27, 2016, 7 pages.
Extended European Search Report for EP Application No. 16275127, dated Oct. 27, 2016, 6 pages
Search Report for GB Application No. GB1813315.7, dated Jan. 25, 2019, 7 pages.
*Symetis ACURATE TF™ aortic bioprosthesis*, published in 2013 in EuroIntervention 2013;9:S107-S110. DOI: 10.4244/EIJV9SSA22.

* cited by examiner 6
24
268
276
274
266
14
230
50
10
232
48
130
146
232
128
2
176
226
8
12
174
152
164
150
4
16
20
18

26
274
268
276
14
280
278
316
266
320
322
312
22
10
50
44
46
42
40
38
36
34
33
214
204
210
166
178
180
8
12
152
164
30
150
16
18

218
220
10
232
130
146
128
226
262
256
234
238
236
237
144
264
136
134
260
247
254
248
132
246
258
244

126
120
122
116

144
142
126
120
132
138
122
116

218
280
320
230
10
220
222
136
134
212
180
216

138
122
116
30
138
32
140
78
82
84
90
96
92
74
122
116
22

22
30
122
116
140
32
84
78
90
122
22
116

30
32
138
148
22
78
90
116
122

24
292
284
290
302
298
298
288
22

286
290
294
298
284
288
298
302

22
30
154
160
186
184
154
152
186
156
162
158
30
150
22

186
160
184
158
184
186
156
154

23
23
210
204
210
206
202
208
166
12
176
164
174

182
166
192
178
160
184
184
186
186
192
158
154
156
188
168
188
12
172
190
170
182
190
164
174

166
170
178
172
12
168
196
194
164
200
198

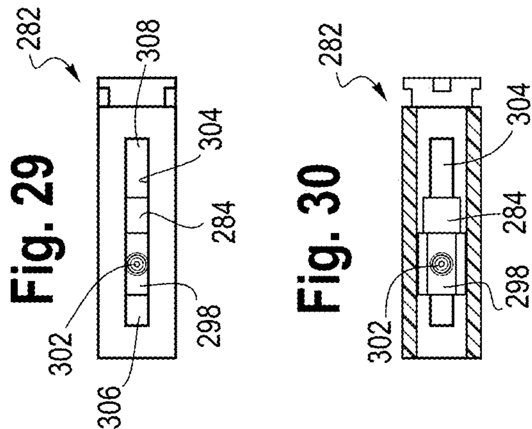
Fig. 29
Fig. 30
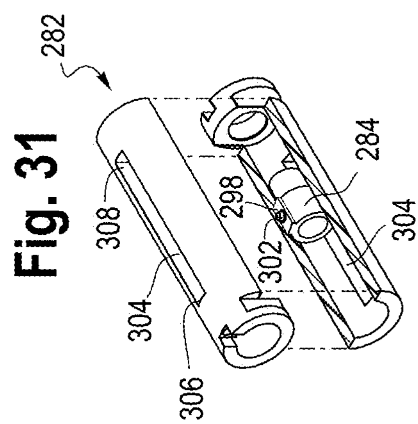
Fig. 31
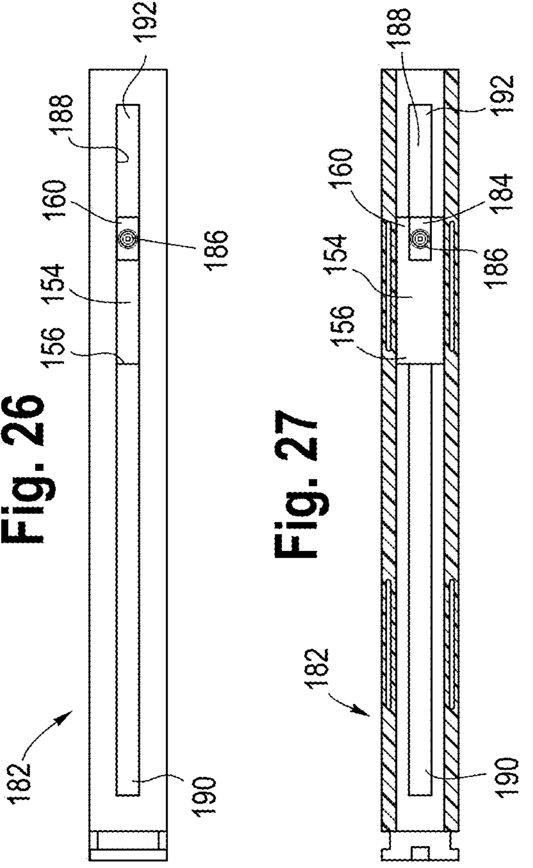
Fig. 26
Fig. 27
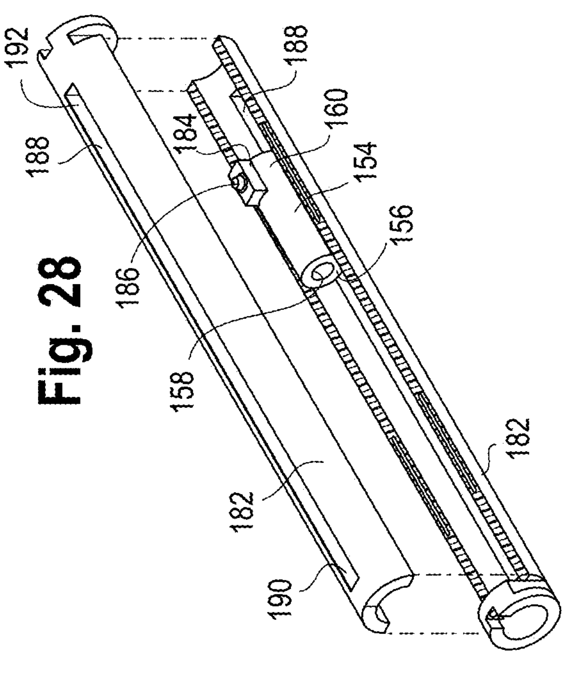
Fig. 28

14
274
276
278
266
316
314
310
318
312
318
318

308
268
274
270
304
290
294
284
302
298
288
294
306
278
14
282
286
272
266

MODULAR HANDLE COMPRISING A TRIGGER WIRE ACTUATION MECHANISM FOR A PROSTHESIS DELIVERY DEVICE

RELATED APPLICATIONS

This application is a continuation of U.S. patent application Ser. No. 18/073,014, filed Dec. 1, 2022, which is a continuation of U.S. patent application Ser. No. 16/419,282, filed May 22, 2019, which is a continuation of U.S. patent application Ser. No. 15/244,501, filed Aug. 23, 2016 (now U.S. Pat. No. 10,335,301), which claims the benefit of the filing date under 35 U.S.C. § 119(e) of Provisional U.S. Patent Application Ser. No. 62/212,767, filed Sep. 1, 2015, which are hereby incorporated by reference in their entireties.

BACKGROUND

This invention relates generally to medical devices and methods of using the same, and more particularly, to an endovascular prosthesis delivery device and methods for placement and deployment of the prosthesis in the lumen of a vessel.

The use of delivery devices or introducers employing catheters has long been known for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, it has also long been known to deliver an implantable medical device by means of a catheter, often intraluminally. For example, a stent, stent-graft, vena cava filter or occlusion device may be delivered intraluminally from the femoral artery, via a transapical approach and/or using other acceptable delivery locations and methods for deployment of the prosthesis.

For procedures in which a prosthesis or other medical device is implanted into a patient, the prosthesis to be implanted is normally held on a carrier catheter or cannula of the introducer in a compressed state and then released from the cannula so as to expand to its normal operating state, prior to withdrawal of the cannula from the patient to leave the implant in position. In many devices, the steps to carry out the implantation my occur, for example, first by retracting a retractable sheath to expand or partially expand the prosthesis, and then performing further steps to, for example, release one or both ends of the prosthesis, deploy an anchoring stent, or the like.

The prosthesis which is to be implanted within a patient's vasculature by the delivery device may vary depending on various factors including the procedure being performed and the portion of the vasculature being treated. The delivery device described herein comprises a modular handle assembly that can be configured to deploy a wide range of different prostheses including, but not limited to cuffs, single lumen tubular stent grafts, bifurcated AAA stent grafts, branched or fenestrated stent grafts and combinations thereof. In addition to facilitating the delivery of a wide range of prostheses, the modular handle also allows a variety of delivery approaches to be utilized, including but not limited to transapical or femoral approaches. More specifically, the modular handle comprises various components that have standardized interfaces, allowing the components to be configured and assembled in differing ways, thus providing a delivery device capable of delivering and deploying a full range of prostheses, thus providing high quality patient care with cost savings in production and manufacture.

While this invention may be generally discussed in relation to a delivery device for a stent graft and method of deployment thereof into one or more specific arteries, including the aorta and iliac arteries, it is also contemplated that the invention is not so limited and may relate to any prosthesis and/or any body or vessel lumen in which such a deployment is necessary or desired.

SUMMARY

The present disclosure describes a handle assembly comprising a trigger wire actuation mechanism for delivering and deploying an endovascular graft into one or more vessels. In one example, a handle assembly for a prosthesis delivery device is disclosed. The handle assembly comprises a stationary main handle having a proximal end and a distal end and an outer surface extending therebetween. A first helical groove is formed in at least a portion of the outer surface of the main handle and a first trigger wire actuation mechanism disposed about the main handle and rotatably moveable relative to the main handle. A first trigger wire is operatively connected to the first trigger wire actuation mechanism, the first trigger wire having a prosthesis capture condition and a prosthesis release condition. Movement of the first trigger wire actuation mechanism causes movement of the first trigger wire thereby moving the first trigger wire from the prosthesis capture condition to the prosthesis release condition.

In another example, the handle assembly may further comprise a second trigger wire actuation mechanism disposed about the main handle and rotatably moveable relative to the main handle. A second trigger wire is operatively connected to the second trigger wire actuation mechanism, the second trigger wire having a prosthesis capture condition and a prosthesis release condition. Movement of the second trigger wire actuation mechanism causes movement of the second trigger wire thereby moving the second trigger wire from the prosthesis capture condition to the prosthesis release condition.

BRIEF DESCRIPTION OF THE DRAWINGS

FIG. 26 is a top view of the first follower disposed within the front rail.

FIG. 27 is a cross-sectional view of the front rail and the first follower disposed therein.

FIG. 28 is an exploded view of the front rail showing the first follower disposed therein.

FIG. 29 is a top view of the second follower disposed within the rear rail.

FIG. 30 is a cross-sectional view of the rear rail and the second follower disposed therein.

FIG. 31 is an exploded view of the rear rail showing the second follower disposed therein.

DETAILED DESCRIPTION

Figure 1:
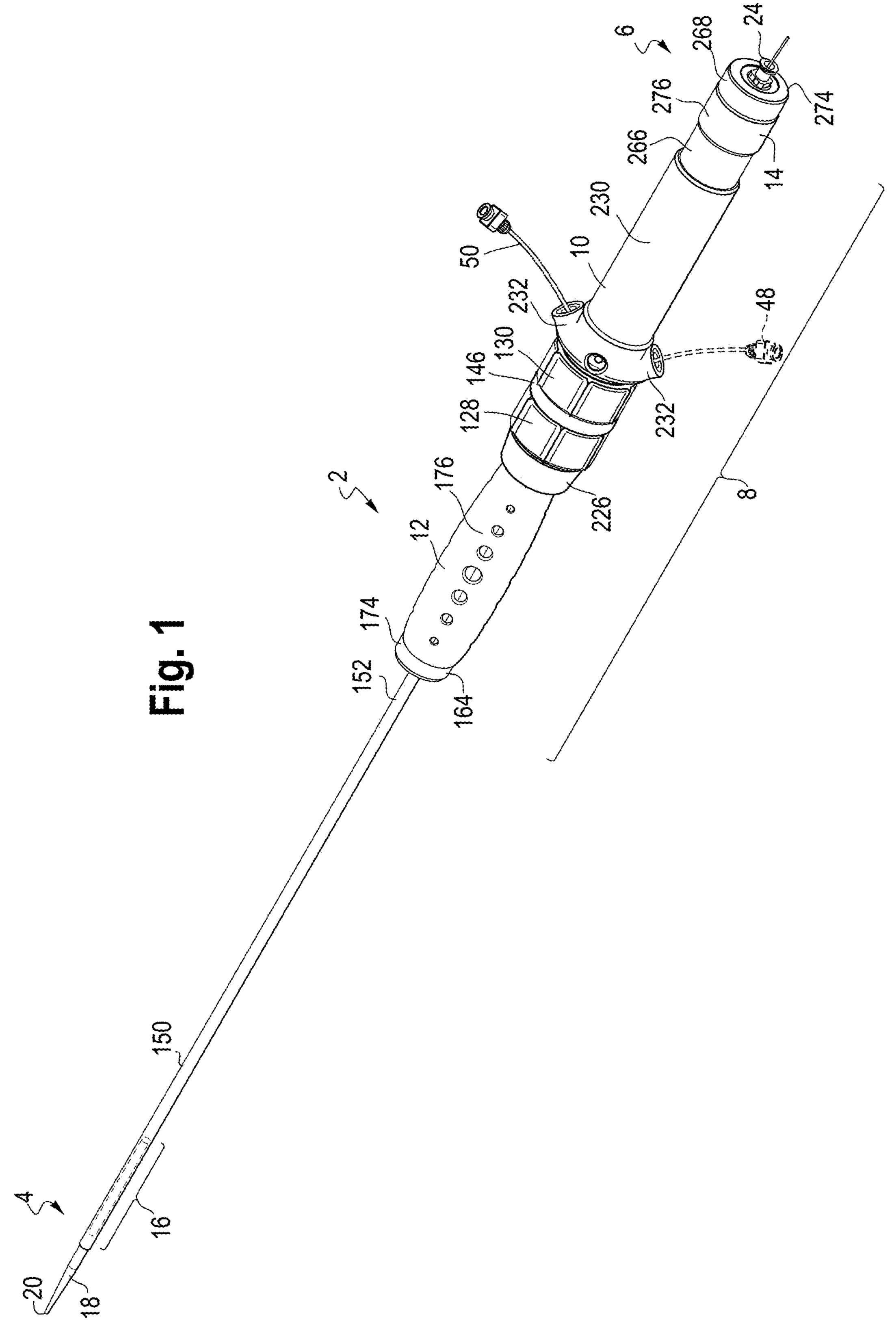
FIG. 1 is a rear perspective view of a delivery device with a handle assembly at the distal end of the device and a prosthesis coupled to the proximal end of the device.

In this description, when referring to a prosthesis delivery device, "proximal" refers to the part of the delivery device that is furthest from the operator and intended for insertion in a patient's body and "distal" refers to that part of the delivery device closest to the operator. With regard to the prosthesis, the term "proximal" refers to that part of the prosthesis that is closest to the proximal end of the delivery device and "distal" refers to the opposite end of the prosthesis. The term "ipsilateral" is used to indicate that the diseased vessel(s) being accessed during a given procedure are on the same side of the body (right or left) as the vascular access delivery device/introducer, while "contralateral" signifies that the vessel(s) of interest are on the opposite side of the body.

In general and described in more detail below with reference to the reference numbers and figures, the delivery device 2 includes a proximal end 4 and a distal end 6 as shown generally in FIGS. 1 and 3. A handle assembly 8 is located adjacent the distal end of the device. As shown in an exploded view in FIG. 2, the handle assembly 8 generally includes first or main handle 10, a second or front handle 12 and a third or rear handle 14. The main handle 10 is fixed relative to the delivery device 2. In one example, the main handle 10 may also be fixed relative to the front handle 12 and/or to the rear handle 14, with the front handle 12 and the rear handle 14 being separately and independently rotatable relative to the main handle 10.

Figure 2:
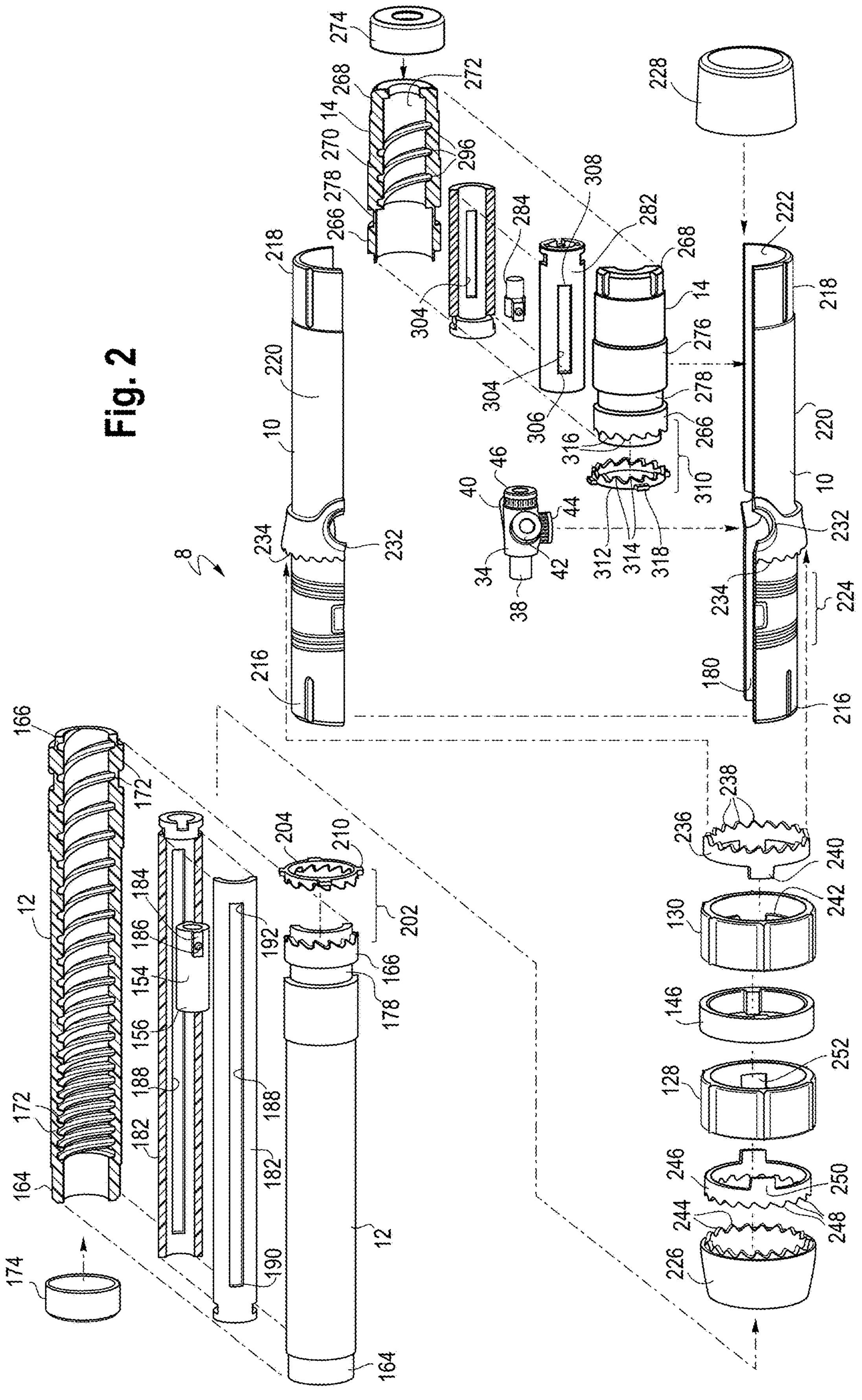
FIG. 2 is an exploded view of one example of a handle assembly.
Figures 3, 4:
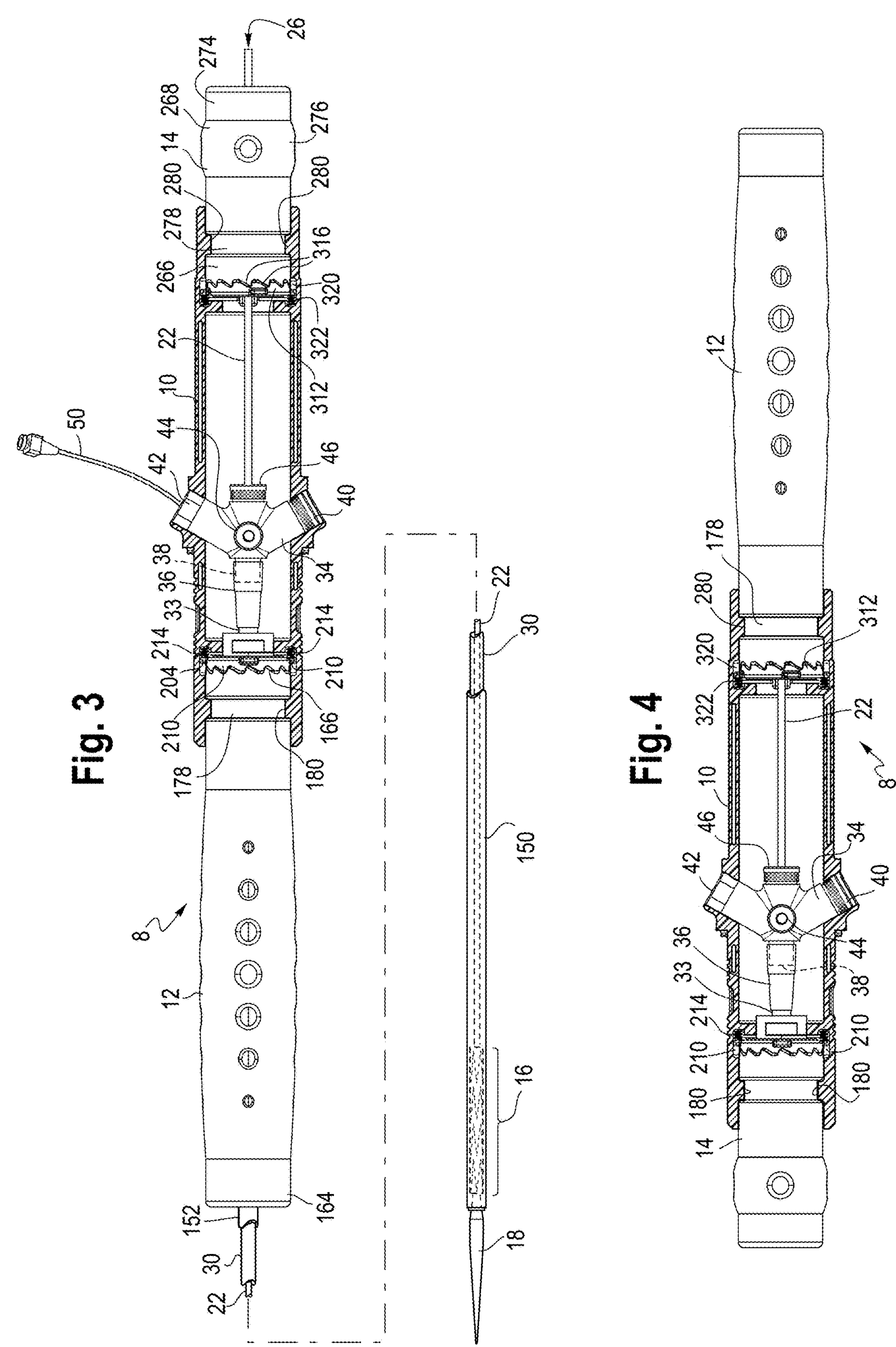
FIG. 3 is one example of a delivery device with a partial cross-sectional view of the handle assembly.
FIG. 4 is a partial cross-sectional view of another example of a handle assembly.

As shown in FIGS. 1, 2 and 3, the front handle 12 extends proximally from the main handle 10 and has a greater longitudinal length than the rear handle 14 which has a relatively shorter longitudinally length and extends distally from the main handle 10. However, the handle assembly 8 may be modular, in that the handle assembly 8 is made up of various parts (including, but not limited to the front handle 12, the main handle 10 and the rear handle 14) that can be assembled, connected or otherwise combined during manufacture in a variety of ways. Accordingly, as shown in FIG. 4, it is also possible to assemble the handle assembly 8 in which the front handle 12 and rear handle 14 are switched, so that the relatively shorter handle 14 extends proximally from the main handle 10 while the relatively longer handle 12 extends distally from the main handle 10. The modular design of the handle assembly 8 allows it to be configured in a variety of ways depending on the procedure being performed and the particular prosthesis that is being delivered using the device. In some procedures it is advantageous to have the longer front handle 12 extending proximally from the main handle 10 and the shorter rear handle 14 extending distally from the main handle as shown in FIG. 3, while in other procedures to deliver a different prosthesis it may be advantageous to configure the modular handle differently, such as is illustrated in FIG. 4, as will be described in further detail below.

In one non-limiting example, if the prosthesis being delivered and deployed has a relatively shorter longitudinal length, then it may be advantageous to provide a handle assembly 8 in which the relatively shorter handle 14 is in front and extends proximally from the main handle 10, while the relatively longer handle 12 extends distally from the main handle 10 as FIG. 4 illustrates.

Figures 5, 6:
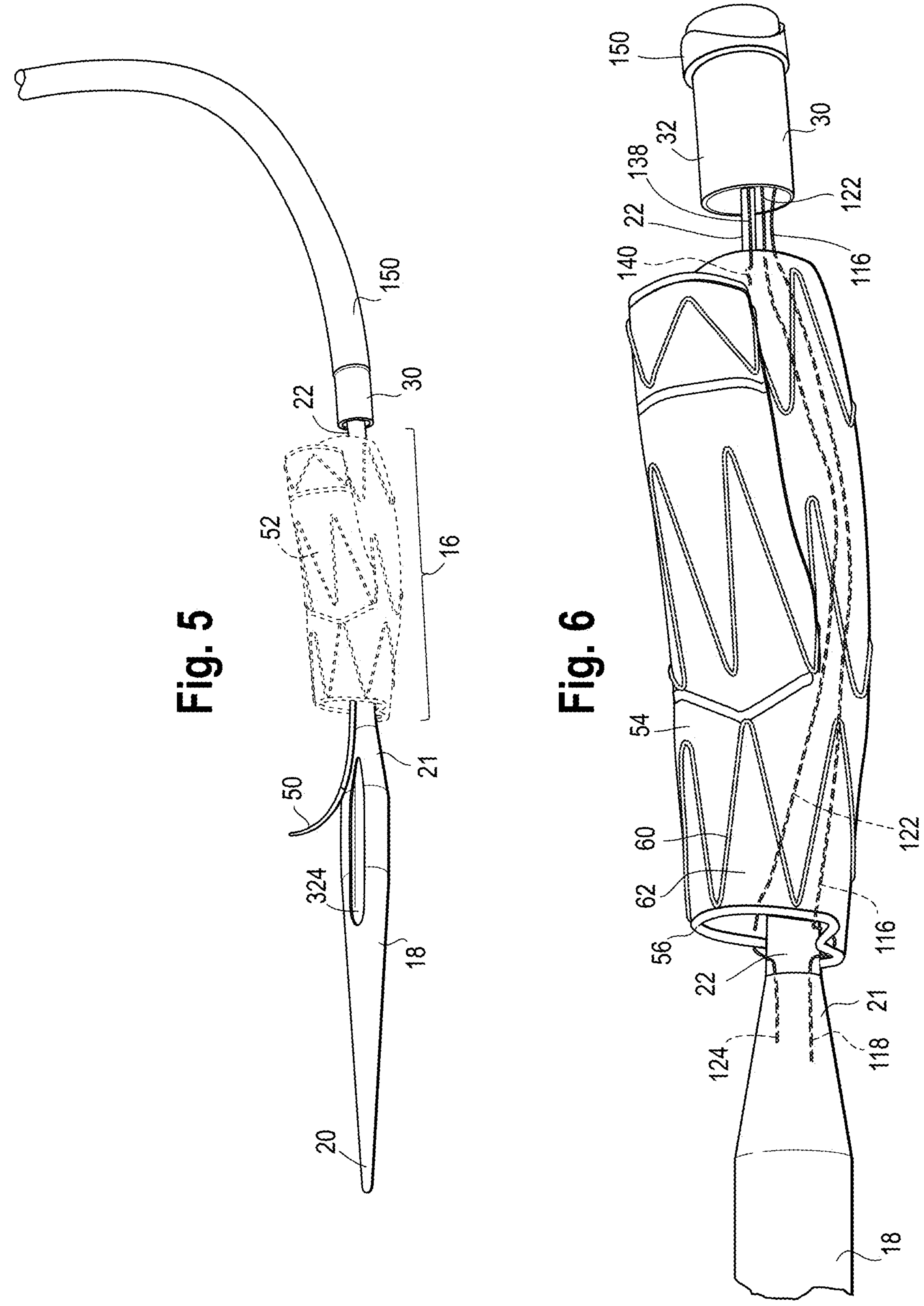
FIG. 5 illustrates the proximal end of the delivery device and one example of a prosthesis releasably coupled thereto.
FIG. 6 is an enlarged view of one example of a stent graft releasably coupled to the proximal end of a delivery device with two proximal trigger wires and one distal trigger wire.

As shown in FIGS. 3, 5 and 6, the proximal end 4 of the delivery device 2 includes retention region 16 upon which a variety of prostheses 52 can be releasably coupled and a tapered nose cone dilator 18 having a proximal tip 20 and a reverse distal taper at its distal end 21. The nose cone dilator 18 presents a smooth tapered surface to facilitate entry into and movement through a body vessel. Nose cone dilator 18 may include radiopaque material or be equipped with a radiopaque marker (not shown) to facilitate visualization of the nose cone dilator 18 in use provided by desired imaging modality (i.e., by fluoroscopy, MRI, 3D or other imaging techniques). An inner cannula 22 extends the longitudinal length of the delivery device 2, from a pin vice 24 at the distal end 6 of the device 2 to the tapered nose cone dilator 18 at the proximal end 4 of the device 2. Inner cannula 22 has an inner lumen 26 which may accommodate a guide wire 28 for tracking the delivery device 2 to a desired position within a patient's vasculature and which may also be used for flushing or injection of fluids as shown in FIG. 3. The inner cannula 22 may be made of a variety of suitable materials that are stiff, yet flexible enough to allow the inner cannula 22 to conform to the tortious anatomy of a patient during use, and may be either straight or have a curve imparted to a portion of it. For example, the inner cannula 22 may be constructed of polymers, metals and/or alloys, including nitinol or stainless steel.

A stiffening cannula, sometimes referred to as a pusher or positioner 30 may be disposed coaxially over at least a portion of the inner cannula 22. The positioner 30 may be constructed from various materials, and in one example, a proximal portion 32 of the positioner which is introduced into the patient may comprise a polymer, sometimes referred to as VRDT (or vinyl radiopaque dilator tubing), plastics, metals, alloys or a combination thereof, whereas a distal portion 33 of the positioner 30 may comprise the same material as the proximal portion 32 of the positioner 30 or it may be a different material including but not limited to plastics, polymers, alloys, metals or a combination thereof, that provide sufficient maneuverability and stiffness to the positioner 30 as necessary and desired. The positioner 30 may extend from a location just distal of the stent-graft retention region 16 coaxial with a length of the inner cannula 22 and terminate at a distal end 33 within the main handle 10.

As shown in FIG. 3 and FIG. 4, the distal end 33 of the positioner 30 may be attached or coupled to a valve 34 located within the main handle 10 by various means, including threaded attachment, adhesives, welding, and/or other suitable attachment mechanisms and a silicone sleeve 36 is disposed over the distal end 33 of the positioner to secure it to a proximal portion of the valve 34. For a length of the positioner 30, a stiffening rod (not shown) may be disposed over the inner cannula 22 and/or over the positioner 30 for additional stability and maneuverability.

The valve 34 has multiple openings or ports. The distal end 33 of the positioner 30 is attached to a proximal port 38. Just distal of the proximal port 38 is a first side port 40 and a second side port 42 which extend radially outwardly from the center of the valve 34. Between the first and second side ports 40, 42 is a central port 44, while a distal port 46 extends rearward from the valve 34. While the valve 34 shown includes at least these five ports 38-46, it is also contemplated the valve 34 may include more or fewer ports as necessary and desired. The ports may serve various purposes during use, depending on the particular procedure being performed, as described below.

As previously mentioned, the positioner 30 is coupled to and extends proximally from the proximal port 38. In a non-limiting example, as shown in FIG. 1, one of the first and second side ports 40, 42 may be used for flushing various fluids in and through the device, such as through an auxiliary catheter 48, while the other of the first and second ports may accommodate a second auxiliary catheter 50, sometimes referred to herein as a "cannulating catheter 50." The second auxiliary catheter 50 or "cannulating catheter" may be used for cannulating a branched or fenestrated stent graft carried by the device and/or for cannulating one or more branch vessels during a procedure as will be described in further detail below. The inner cannula 22 extends longitudinally through the valve 34 passing through the proximal port 38 and the distal port 46. The central port 44 may provide a passage for one or more trigger wires or diameter reducing ties as will be described in further detail below.

Each of the respective ports of valve 34 may be male or female, may be threaded either on the inner surface or outer surface thereof, thereby facilitating the attachment and/or coupling of one or more secondary devices, including but not limited to catheters, tubing, wires, or other devices that may be necessary to couple and/or to introduce into or through any one of the ports during a procedure. Each of the respective ports may also contain a seal (not shown) therein to prevent back flow of fluid or unintended leakage through the ports. The seal(s) may be rings, discs or other suitable valving mechanisms made from silicones, rubbers, plastics or other materials.

Figure 9:
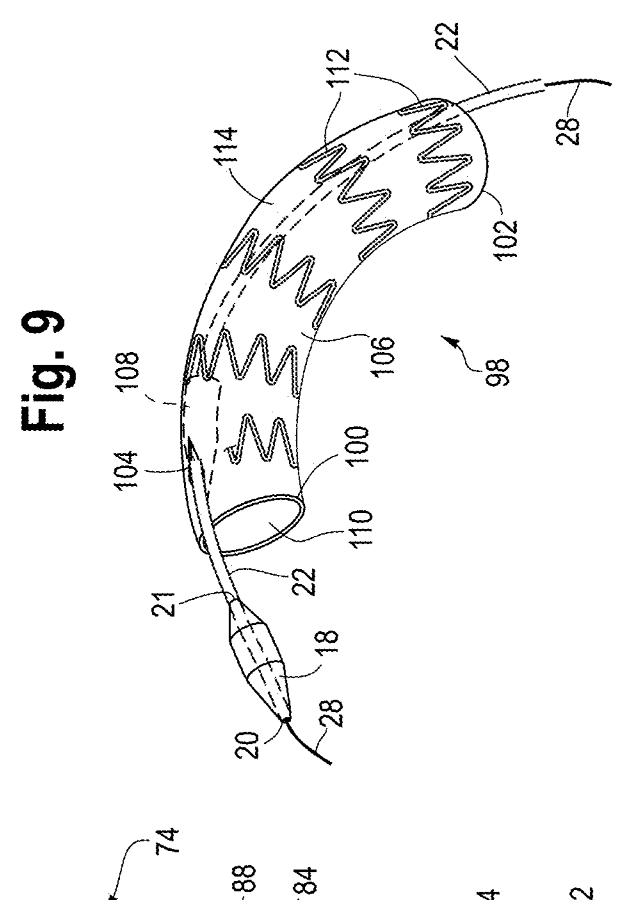
FIG. 9 is another exemplary stent graft that may be delivered and deployed within the vasculature of a patient.
Figure 8:
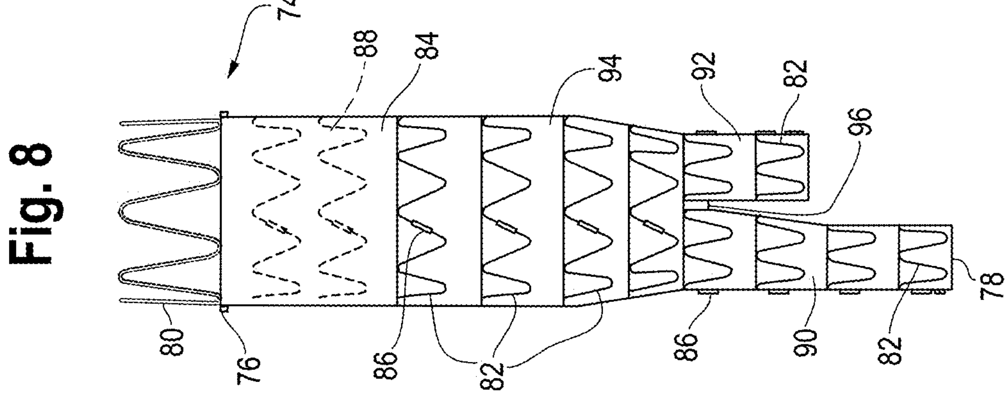
FIG. 8 is another exemplary stent graft that may be delivered and deployed within the vasculature of a patient.
Figure 7:
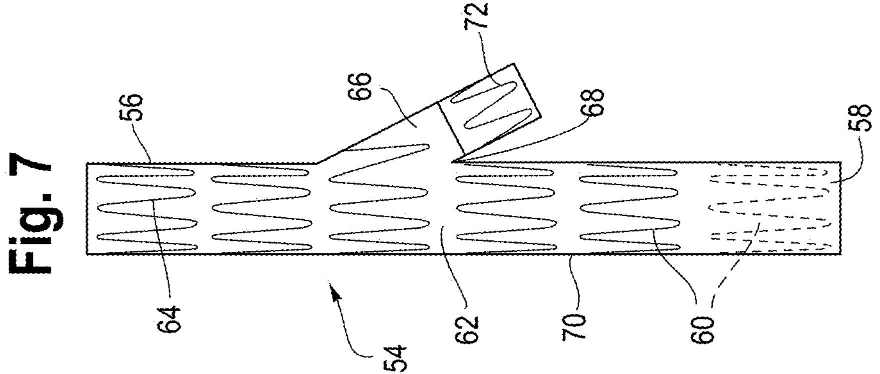
FIG. 7 is an exemplary stent graft that may be delivered and deployed within the vasculature of a patient.

Referring now to FIGS. 7, 8 and 9, at least three exemplary prostheses 52 are shown, which may be delivered to and deployed within a patient in a controlled and sequential manner using the delivery device 2 described herein. As previously mentioned, the modular handle assembly 8 can be configured to deliver and deploy a wide variety of prostheses 52, including variously sized and shaped stent grafts, and as such, FIG. 5 illustrates one exemplary prosthesis 52 in dashed lines to indicate that it is a generic prosthesis for illustrative purposes and that any one or more different prostheses can be interchanged with stent graft 52 and be releasably coupled to the proximal end of the inner cannula 22 in a similar fashion. As such, the prostheses 52 shown in FIGS. 7, 8 and 9 are only several examples of a wide range of prostheses that can be introduced into a patient's vasculature and deployed therein with the device 2.

Turning to FIG. 7, one example of a stent graft 54 is shown, which may be releasably coupled to the prosthesis retention region 16 of the delivery device 2. The stent graft 54 has a proximal end 56, a distal end 58, and a series of stents 60 extending the length of the stent graft 54 and attached to the graft material 62. The proximal end 56 of the stent graft 54 may include a sealing stent 64. Sealing stent 64 may be internal or external to the graft material 62. A series of body stents 60 also are attached to the graft material 62 and may be sutured to the graft material or held to the graft material in other known ways. The series of body stents 60 may be internal or external to the graft material 62, or both. As shown in FIG. 7, all of the stents are external to the graft material 62 with the exception of the distal-most stent which is internal to the graft material 62.

As shown in FIGS. 6 and 7, the stent graft 54 may comprise a side arm or limb 66 extending from the tubular main body 70. The side arm 66 may be integrally formed with the main tubular body 70 and extend from the tubular main body at bifurcation 68. Alternatively, the side arm 66 may be separately formed and attached to the main tubular body 70, and in one example, the side arm 66 may extend from a fenestration (not shown) formed in the wall of the main tubular body 70 as shown in FIG. 3. The side arm 66 may also include one or more stents 72 along its length, either internal or external or both. Although FIGS. 6 and 7 show a stent graft 54 having a single side arm 66 extending therefrom, the stent graft 54 may also be a single non-bifurcated tube and/or the stent graft may have one or more fenestrations formed in the graft material 62 and/or one or more additional side branches or arms extending therefrom. Radiopaque markers (not shown) may be placed on various parts of the stent graft 54 to aid in tracking and locating the device at a desired location during a procedure and one or more barbs (not shown) may extend from any one of the body stents 60 or the sealing stent 64 to help anchor the stent graft 54 to the vessel wall. In one non-limiting example, the main body 70 of the stent graft 54 shown in FIG. 7 is configured for delivery to and deployment within the common and external iliac arteries, while the side arm 66 is configured to extend towards and/or into the internal iliac artery.

Referring now to FIG. 8, another exemplary stent graft 74 that can be delivered and deployed using device 2 is shown. The stent graft 74 in FIG. 8 is releasably coupled to the inner cannula 22 at the prosthesis retention region 16. The stent graft 74 also has a proximal end 76 (that end with the bare stent 80 extending therefrom), a distal end 78, and a series of stents 82 extending the length of the stent graft 74 and attached to the graft material 84. Extending from the proximal end 76 of the stent graft 74 is an exposed or bare anchoring stent 80. Anchoring stent 80 is attached to the graft material 84 by, for example, suturing the distal apices of the anchoring stent 80 to the graft material 84. Anchoring stent 80 may have one or more barbs (not shown) for attaching the stent graft 74 to a body vessel. Radiopaque markers 86 may be placed on various parts of the device to aid in visualizing the position of the stent graft 74 during a procedure.

Next, just distal to the bare stent 80 is one or more sealing stents 88. Sealing stent(s) 88 may be internal or external to the graft material 84. The series of body stents 82 also are attached to the graft material 84 and may be sutured to the graft material or held to the graft material in other known ways. The series of body stents 82 may be internal or external to the graft material 84, or both. As shown in FIG. 8, the sealing stent 88 is internal and body stents 82 are external to the graft material 84. As shown in FIG. 8, stent graft 74 is bifurcated having two limbs 90, 92 extending from the tubular main body 94 at bifurcation 96. One of the limbs 92 may be shorter than the other limb 90, or both may be the same length. Limbs 90 and 92 may also have a series of stents 82 along their length, either internal or external, or both. The stent graft 74 illustrated in FIG. 8 may, in one non-limiting example, be configured for placement within the abdominal aorta, with bifurcation 96 seated adjacent to the aortic bifurcation and each of the respective limbs 90, 92 extending distally towards the common iliac arteries.

Turning to FIG. 9, another non-limiting example of a stent graft 98 that can be delivered and deployed using device 2 is shown. The stent graft 98 in FIG. 9 may be releasably coupled to the inner cannula 22 at the prosthesis retention region 16. The stent graft 98 may be a generally singular tube-like configuration having a proximal end 100 and a distal end 102 and may comprise one or more openings or fenestrations 104 formed in the graft body 106. There may also be an internal side branch 108 extending within the lumen 110 of the graft body 106 as illustrated in FIG. 9 although other configurations are also contemplated. A series of stents 112 may be attached to the graft body 106 and extend along all of, or at least part of, the length of the stent graft 98. The stents 112 may be sutured to the graft material 114 or held to the graft material 114 in other known ways. The series of body stents 112 may be internal or external to the graft body 106, or both. Radiopaque markers (not shown) may be placed on various parts of the stent graft 74 to aid the user in positioning the stent graft during deployment. The stent graft 74 shown in FIG. 9 may, in one example, be configured for delivery to and deployment within the aorta, with the fenestration 104 and/or internal side branch 108 at least partially aligned with one or more branch vessels extending from the aortic arch, including but not limited to the brachiocephalic artery, the left common carotid artery and/or the left subclavian artery.

The stents connected to any of the stent grafts described above may be zig-zag shaped as shown in the figures, although other stent configurations are known and may be used alone or in combination with the zig-zag stents and/or have other configurations as known in the art. The stents may be constructed of a self-expanding shape memory material, such as Nitinol, or they may be balloon expandable, or a combination of both depending on the particular characteristics desired of the prosthesis 52.

An exemplary coupling of the prosthesis 52 to the delivery device is shown in FIG. 6 (including any one of the above described prostheses) although other prostheses not specifically described herein may also be releasably coupled to the delivery device depending on the particular procedure being performed. In fact, the modular handle assembly 8 described herein is designed so as to be able to be configured in a variety of ways to facilitate the delivery of a full range of prostheses, including but not limited to the full line of endovascular prostheses offered by Cook Medical Technologies LLC of Bloomington, Indiana, for example.

FIGS. 5 and 6 illustrate a proximal end portion 4 of the delivery device 2 and one non-limiting example of an attachment and release mechanism for the proximal end of a stent graft 52. For exemplary purposes only, reference numbers used for the branched iliac stent graft 54 shown in FIG. 7 will be used, but the same attachment and release mechanism can be used for any prosthesis 52 if desired. The attachment and release mechanism can be operated and manipulated using the handle assembly 8 described herein. The description of the coupling of stent graft 52 to the delivery device 2 is for exemplary purposes, and shall not be considered limiting, as different prostheses may be releasably coupled to the delivery device in different ways, and the proximal end and distal end of a particular prosthesis may be coupled to the delivery device in different ways.

As shown in FIG. 6 an exemplary prosthesis attachment mechanism releasably couples the proximal end 56 of the stent graft 54 to the inner cannula 22. In a non-limiting example, as shown in enlarged view in FIG. 6, the attachment mechanism comprises at least one proximal trigger wire 116 having a proximal end 118 and a distal end 120 (see FIG. 12). However, other attachment mechanisms, including an additional proximal trigger wire 122 also having a proximal end 124 and a distal end 126 (see FIG. 12) may also be used to releasably couple the proximal end 56 of the stent graft 54 to the inner cannula 22. Other attachment mechanisms, in addition to the one or more proximal trigger wires 116, 122, may also be used to couple the proximal end 56 of the stent graft 54 to the delivery device 2, such as diameter reducing ties, a retractable sheath, sutures and the like as will be recognized by one of skill in the art. U.S. application Ser. No. 13/970,861 filed on Aug. 20, 2013, describes one example of a releasable diameter reducing tie, which is incorporated by reference herein in its entirety.

Figures 10, 11:
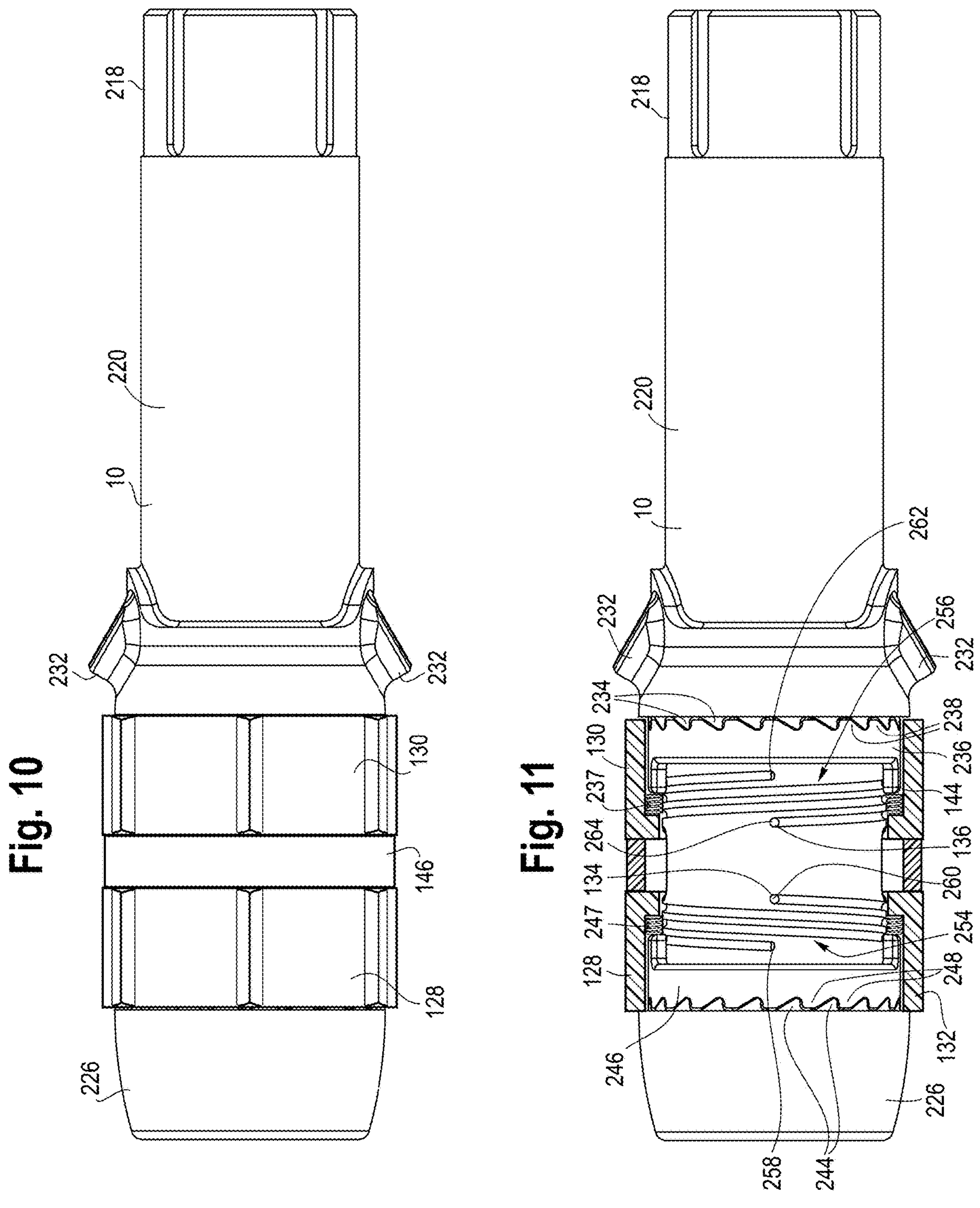
FIG. 10 is a side view of the main handle with a first rotating trigger wire release knob and a second rotating trigger wire release knob disposed about the main handle.
FIG. 11 is a partial cross-sectional view of the main handle of FIG. 10.
Figures 12, 13, 14:
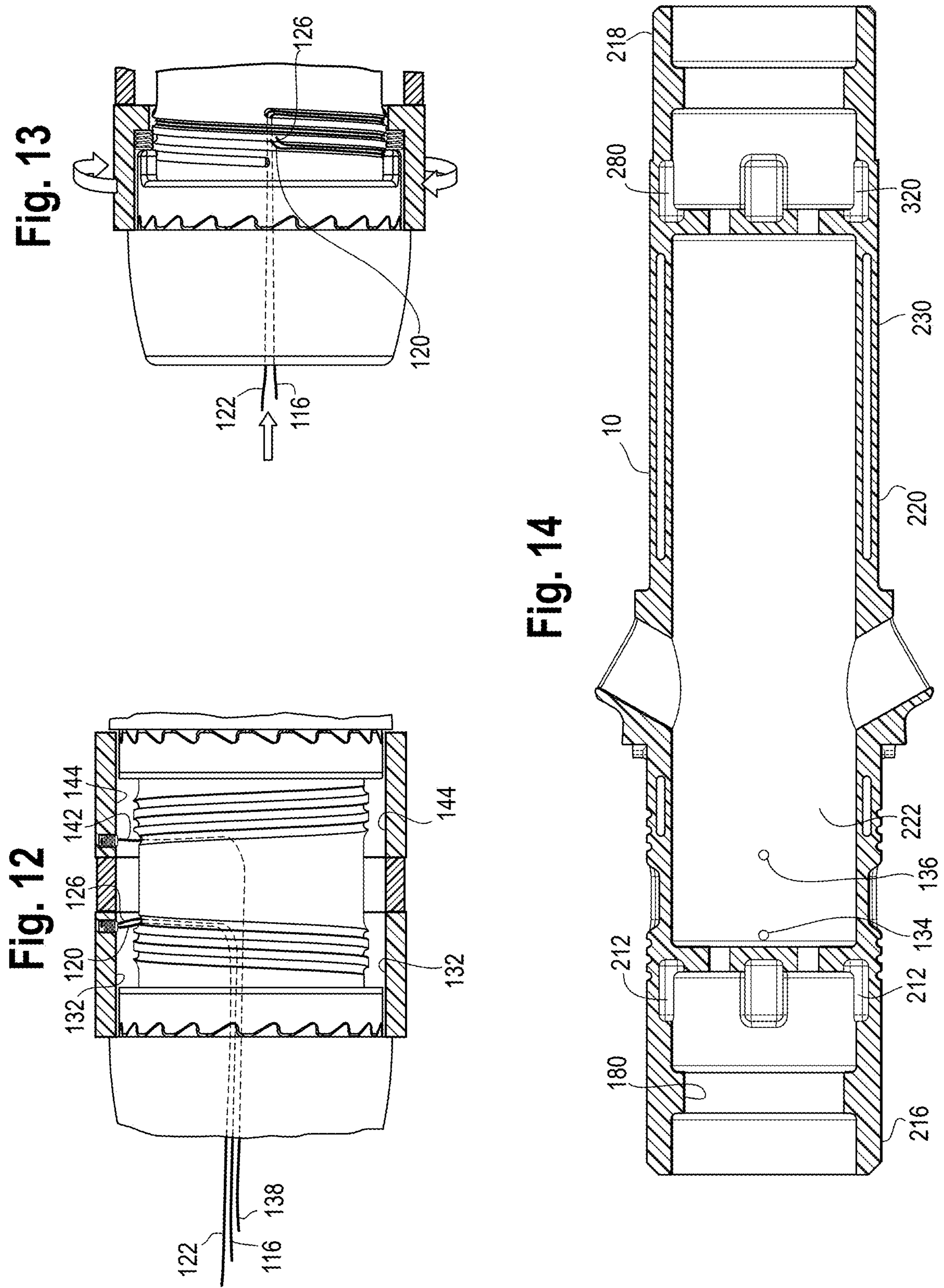
FIG. 12 is a cross-sectional view of the first and second trigger wire release knobs of FIG. 10 with the distal ends of the trigger wires secured to the inner surface of the respective knobs.
FIG. 13 is a cross-sectional view of the first rotating trigger wire release knob and the proximal trigger wires wrapping upon the outer surface of the main handle as the knob is rotated.
FIG. 14 is a cross-sectional side view of the main handle with the first and second rotating trigger wire release knobs removed.

In one non-limiting example, the proximal trigger wires 116 and 122 may extend proximally within positioner 30 from the handle assembly 8 to the proximal end 56 of the stent graft. More particularly, the distal ends 120, 126 of the proximal trigger wires 116, 122 may be coupled to the inner surface of one or more trigger wire release mechanisms or rotatable rings 128, 130 that are disposed about and/or around at least a portion of the main handle 10 (as will be described in further detail below in connection with FIGS. 10-13). In one example, the distal ends 120, 126 of the proximal trigger wires 116, 122 may be coupled to the inner surface 132 of the first or proximal rotatable ring 128 by a set screw, by adhesives, welding or any other suitable attachment mechanisms as shown in FIG. 12. From the attachment point on the inner surface 132 of the first rotatable trigger wire ring 128, the proximal trigger wires 116, 122 extend through one or more openings or apertures 134, 136 formed in the main handle 10, shown in FIG. 14. For example, as shown in FIGS. 11, 12 and 14, main handle 10 has two spaced apart apertures 134, 136 through which one or both of the proximal trigger wires 116, 122 may extend through and into the interior housing of main handle 10. In one example, both of the proximal trigger wires 116, 122, extend through one of the holes 134 or 136, or alternatively, one of the proximal trigger wires 116, 122 can extend through one of the holes 134 or 136 formed in the main handle 10 while the other of the proximal trigger wires 116, 122 extend through the other hole 134 or 136. The proximal trigger wires 116, 122 may then extend through one of the ports of the valve 34 such as the central port 44. The proximal trigger wires 116, 122 can then extend proximally through the valve 34 and exit the valve through the proximal port 38 and extend further proximally through the positioner 30 to the proximal end 56 of the stent graft 54 as shown in FIG. 6. The proximal ends 118, 124 of the trigger wires 116, 122 are releasably coupled to the proximal end 56 of the stent graft 52 as shown in FIG. 6.

In one example, the proximal trigger wires 116, 122 may be directly or indirectly attached to the proximal end 56 of the stent graft 52. For example, the proximal trigger wires 116, 122 may engage a suture loop (not shown) which is attached to the proximal end 56 of the stent graft 54. In this way, the trigger wires do not weave directly through the graft material 62. Alternatively, the proximal trigger wires 116, 122 may be woven directly through or removably attached to the graft material 62 or woven over or through one or more stents 60 at the proximal end 56 of the graft 54. As FIG. 6 shows, the proximal trigger wires 116, 122 are woven directly through the graft material 62 at the proximal end 56 of the stent graft 54 at two spaced apart points around the periphery of the tubular graft body such that when those points are retained by the trigger wires 116, 122 against the inner cannula 22, the stent graft 54 generally forms a “figure 8” formation with one lobe of the “figure 8” being slightly larger than the other lobe of the “figure 8.” Of course, other points of attachment may also be used to releasably couple the stent graft 54 to the inner cannula 22 to form various configurations at the proximal end 56 of the stent graft 54. Again, branched iliac stent graft 54 is used for exemplary purposes only in this particular description of proximal stent graft attachment, but any type of prosthesis can be releasably coupled to the inner cannula in this manner. In the event that a stent graft such as that shown in FIG. 8 is coupled to the delivery device, the one or more trigger wires my weave over and/or through the proximal bare stent 80 to releasably couple the proximal end of the stent graft 74 to the inner cannula 22.

As FIG. 6 shows, the proximal ends 118, 124 of the trigger wires 116, 122 may be retained within the distal end 21 of the nose cone, such as by friction fit or other suitable attachment means that allow for the trigger wires to be pulled distally and released from the inner cannula 22 when deployment of the proximal end of the stent graft 52 is necessary or desired. Other suitable attachment methods or mechanisms may be used to removably attach the proximal trigger wires 116, 122 to the proximal end of the stent graft 52 as would be recognized by one of skill in the art. In one non-limiting example, the proximal end of the inner cannula 22 may include a covering or sleeve (not shown) disposed over at least a portion of it, with the sleeve extending proximally from the proximal end 32 of the positioner 30, through the stent graft lumen and to the distal end 21 of the nose cone dilator 18. The sleeve may be silicone, vinyl, rubber, nylon and/or other suitable materials that snugly fit over and around and coaxial with the inner cannula 22.

After exiting the proximal end 32 of the positioner 30, the proximal ends 118, 124 of the proximal trigger wires 116, 122 may extend through at least a portion of the sleeve, exit the sleeve through one or more openings or apertures, weave through the proximal end of the graft 52 (or over one or more stents or suture loops at the proximal end of the stent graft 52) and then the proximal trigger wires 116, 122 can extend back through the sleeve where the proximal ends 118, 124 of the proximal trigger wires 116, 122 can be releasably retained, such as by friction fit, between the inner surface of the sleeve and the outer surface of the inner cannula 22. In other words, if present, the sleeve provides a mechanism for the proximal ends 118, 124 of the proximal trigger wires 116, 122 to be releasably retained in a position against the inner cannula 22, thus holding the proximal end of the stent graft 52 in a radially inwardly contracted delivery configuration.

When deployment is desired, distal retraction of the proximal trigger wires 116, 122, (such as by manipulation of one or both of trigger wire release mechanisms or rotatable rings 128, 130 as will be described in further detail below) allows the proximal ends 118, 124 of the proximal trigger wires 116, 122 to be released from the proximal end of the stent graft 52 and pulled distally through the positioner 30, allowing the proximal end of the stent graft 52 to at least partially deploy radially outwardly within a vessel. If other diameter reducing ties are being used to radially restrain the proximal end of the stent graft 52, those ties must also be removed by manipulation of one or both of the trigger wire release mechanisms or rotatable rings 128, 130 to allow the proximal end of the stent graft to fully deploy from the inner cannula 22 within the vessel.

As shown in FIGS. 6, and 15-17, various exemplary prosthesis attachment mechanism releasably couples the distal end of a stent graft 52 to the inner cannula 22. In a non-limiting example, the long leg 90 of the abdominal aorta stent graft 74 of FIG. 8 is used for exemplary purposes to illustrate the distal attachment mechanism, and as shown in enlarged view in FIGS. 15-17, the attachment mechanism comprises at least one distal trigger wire 138 having a proximal end 140 and a distal end 142 (see FIG. 12). However, other attachment mechanisms, including an additional distal trigger wire may also be used to releasably couple the distal end of the stent graft 52 to the inner cannula 22. The distal attachment mechanism can be operated and manipulated using the handle assembly 8 described herein. The description of the coupling of the distal end of the stent graft 52 to the delivery device 2 is for exemplary purposes, and shall not be considered limiting, as different prostheses may be releasably coupled to the delivery device in different ways, and the proximal end and distal end of a particular prosthesis may be coupled to the delivery device in different ways.

In one non-limiting example, the distal trigger wire 138 may extend from the handle assembly 8, within positioner 30, to the distal end of the stent graft 74. More particularly, the distal end 142 of the distal trigger wire 138 may be coupled to the inner surface 132 of the first rotatable ring 128, or alternatively, may be coupled to the inner surface

144 of a second trigger wire release mechanism or distal rotatable ring 130 that is disposed about and/or around at least a portion of the main handle 10 just distal to the first or proximal rotatable trigger wire release ring 128 as shown in FIGS. 10-12. The distal rotatable ring 130 may be adjacent to or abut the first rotatable ring 128 or, as shown in FIG. 10, a spacer element, such as a stationary spacer ring 146 may be positioned between the first and second rotatable rings 128, 130. If present, the stationary spacer ring 146 may be coupled to the outer surface of the main handle 10 such as by adhesives, bonding, snap-fit, screws or other suitable attachment mechanisms. The presence of a spacer ring 146 may reduce the risk of the user inadvertently rotating the first rotatable ring 128 and the second rotatable ring 130 at the same time, if simultaneous rotation of the respective rotatable rings is not desired.

The distal end 142 of the distal trigger wire 138 may be coupled to the inner surface 144 of the second rotatable ring 130 by a set screw (see FIG. 12), by adhesives, welding or any other suitable attachment mechanisms. From the attachment point on the inner surface 144 of the second rotatable ring 130, the distal trigger wire 138 extends through one or more openings or apertures 134, 136 formed in the main handle 10. In one example, the distal trigger wire 138 may extend through one of the same holes 134, 136 through which one or both of the proximal trigger wires 116, 122 extends, or alternatively, the distal trigger wire 138 can extend through one of the other holes 134, 136 formed in the main handle 10. The distal trigger wire 138 may then extend through one of the ports of the valve 34 such as the central port 44. The distal trigger wire 138 can then extend proximally through the valve 34 and exit the valve through the front port 38 and extend further proximally through the positioner 30 to the distal end of the stent graft 52.

Figures 15, 16, 17:
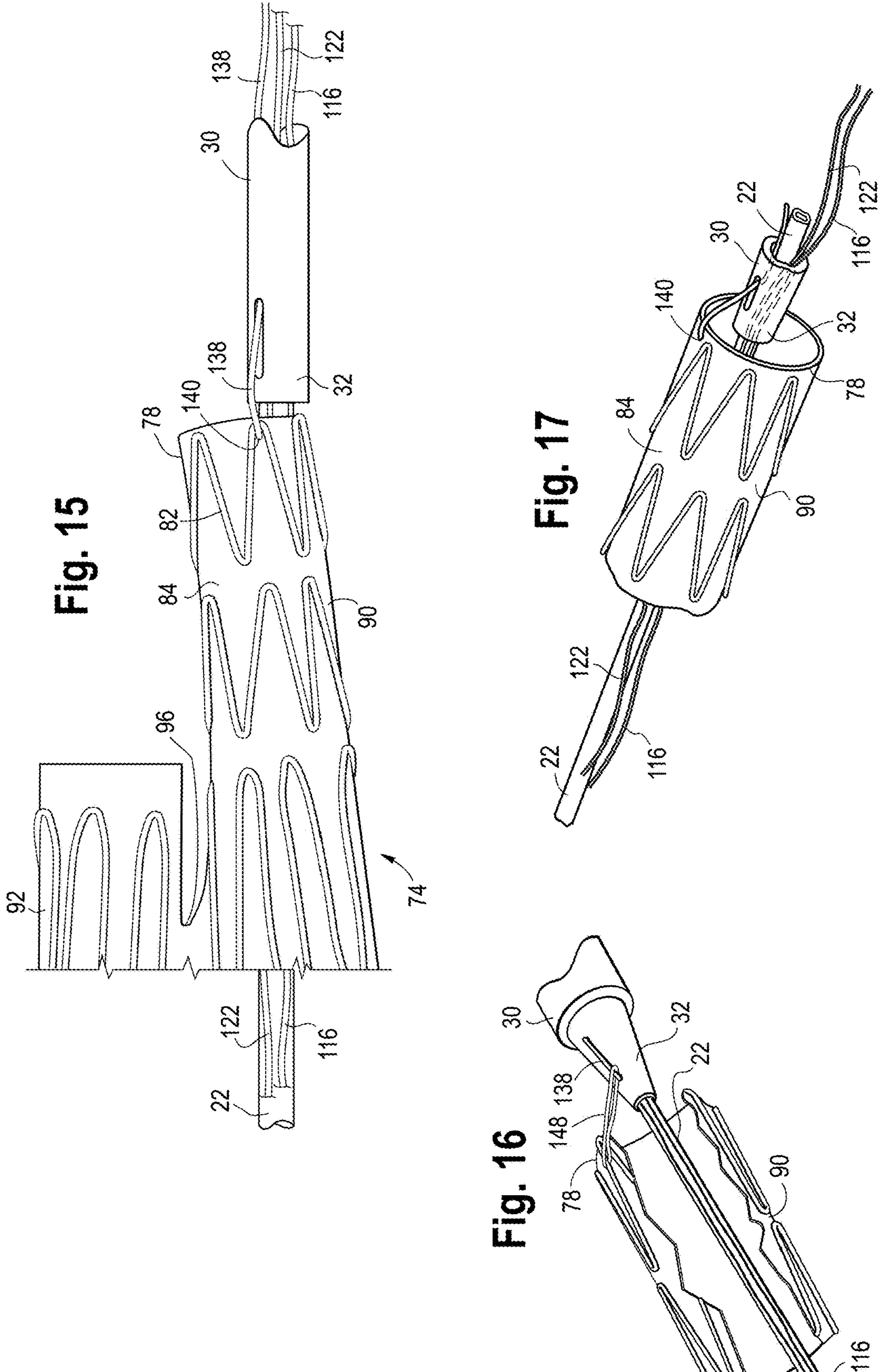
FIG. 15 is one example of a distal trigger wire releasably coupled to the distal end of a stent graft.
FIG. 16 is another example of a distal trigger wire releasably coupled to the distal end of a stent graft.
FIG. 17 is another example of a distal trigger wire releasably coupled to the distal end of a stent graft.

The proximal end 140 of the distal trigger wire 138 may be directly or indirectly attached to the distal end 78 of the stent graft 74. For example, the distal trigger wire 138 may engage a suture loop 148 which is attached to the distal end 78 of the stent graft 74 as shown in FIG. 16. Alternatively, the distal trigger wire 138 may be woven directly through or removably attached to the graft material 84 or may be woven around or over one or more stents 82 at the distal end of the graft 74 as shown in FIGS. 15 and 17. Other suitable attachment methods or mechanisms may be used to removably attach the distal trigger wire 138 to the distal end of the stent graft 74, thereby coupling the stent graft to the inner cannula until the trigger wire(s) are released during deployment, as would be recognized by one of skill in the art.

As shown in FIG. 6, a prosthesis, such as stent graft 52, is disposed on the inner cannula 22 at the proximal end 4 of the delivery device 2 at prosthesis retention region 16. The stent graft 52 has an uncoupled state in which the graft is positioned coaxially over the inner cannula 22 with the proximal end of the stent graft 52 in longitudinal proximity relative to the distal end 21 of the nose cone dilator 18. During assembly, the proximal ends 118, 124 of the proximal trigger wires 116, 122 and the proximal end 140 of the distal trigger wire 138 can be coupled to the respective proximal and distal ends of the stent graft 52 as generally described above. After being coupled to the stent graft 52, the proximal ends 118, 124, of the trigger wires 116, 122 may extend proximally into the nose cone, or alternatively, extend back into the inner cannula 22 through one or more apertures (not shown) formed in the inner cannula or extend back into the sleeve (not shown) that is coaxial with the inner cannula 22.

The proximal ends 118, 124 of the proximal trigger wires 116, 122 may be releasably held in place there, either within the nose cone or within the inner cannula lumen or within the sleeve by friction fit, adhesives or by other releasable attachment mechanisms. When deployment of the stent graft is desired, retraction of the proximal trigger wires 116, 122 and retraction of the distal trigger wire 138 (along with any other additional diameter reducing ties, etc.) by manipulating one or both of the trigger wire release mechanisms or rotatable rings 128, 130 on the handle assembly 8, allows the stent graft 52 to move from a radially inwardly constrained delivery configuration to a radially outwardly expanded configuration within a vessel, as described further below.

The coupling shown in FIG. 6 releasably secures the stent graft 52 to the inner cannula 22 to radially inwardly restrain the stent graft 52 in a manner that may subsequently facilitate insertion of the subassembly comprising the inner cannula 22 and the stent graft 52 into an outer sheath, such as sheath 150 described below. As will be apparent, the outer sheath 150 is configured to radially restrain other regions of the stent graft 52 for delivery in a low-profile configuration to a target site within a patient's anatomy.

Figures 18, 19, 20, 21:
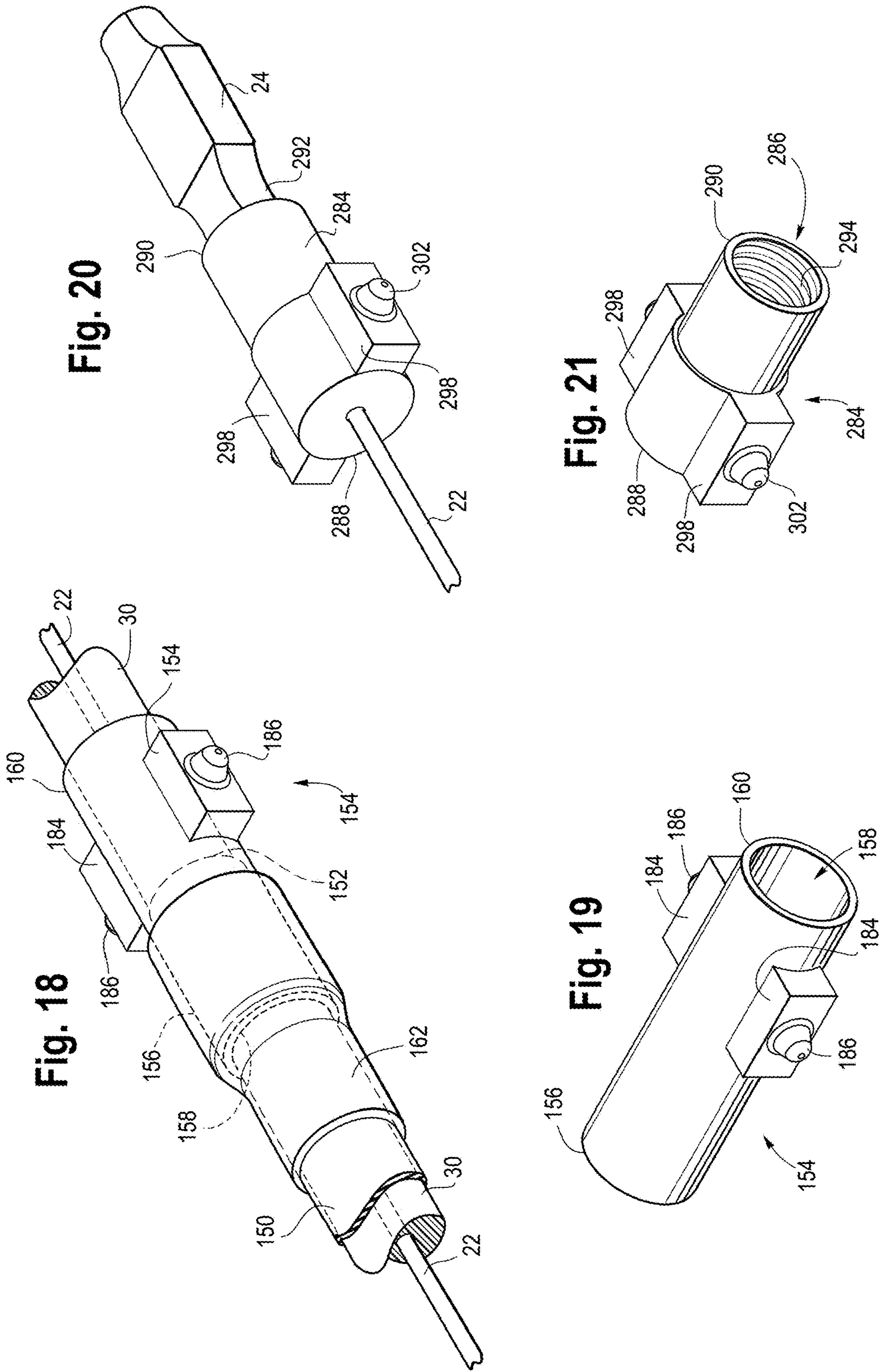
FIG. 18 is a front perspective view of one example of the first follower with a positioner and inner cannula extending longitudinally there through and a sheath secured to the proximal end of the first follower.
FIG. 19 is a rear perspective view of the first follower.
FIG. 20 is a front perspective view of one example of the second follower with an inner cannula extending there through and a pin vice secured to the distal end thereof.
FIG. 21 is a rear perspective view of the second follower.

As shown in FIGS. 1 and 3, the longitudinally slideable and retractable sheath 150 extends along the length of the delivery device 2 from the front handle 12 to the nose cone dilator 18. The sheath 150 is configured to cover and assist in retaining a prosthesis, such as stent graft 52, in a radially inwardly compressed, low-profile configuration during delivery of the prosthesis to a target site within a patient's anatomy. The distal end 152 of the sheath 150 is connected within the front handle 12 to a first follower 154, as shown in FIG. 18. In one example, the distal end 152 of the sheath 150 may be slightly tapered to facilitate attachment of the sheath 150 within a correspondingly shaped proximal end 156 of the first follower 154 as shown in FIG. 18, or the sheath 150 may be flared to fit about the outer surface of the proximal end 156 of the first follower 154. The distal end 152 of the sheath 150 may be secured to the proximal end 156 of the first follower 154 by a friction fit, threaded engagement, adhesives or other attachment mechanisms or combination thereof. The first follower 154 has at least one lumen 158 extending from its proximal end 156 to its distal end 160 as shown in FIGS. 18 and 19 which allows for the positioner 30 to extend longitudinally there through. A sleeve 162 may be disposed over both the distal end 152 of the sheath 150 and the proximal end 156 of the first follower 154 so as to secure the respective components to each other and to prevent the distal end 152 of the sheath 150 from separating or otherwise detaching from the first follower 154.

Figure 22:
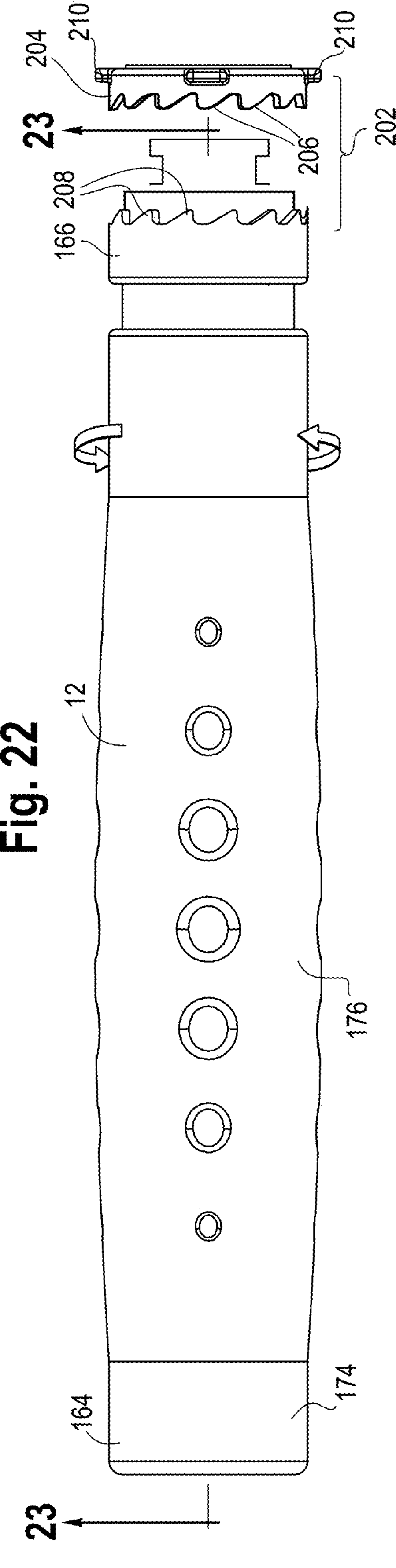
FIG. 22 is a side view of the front handle and ratcheting mechanism.
Figure 23:
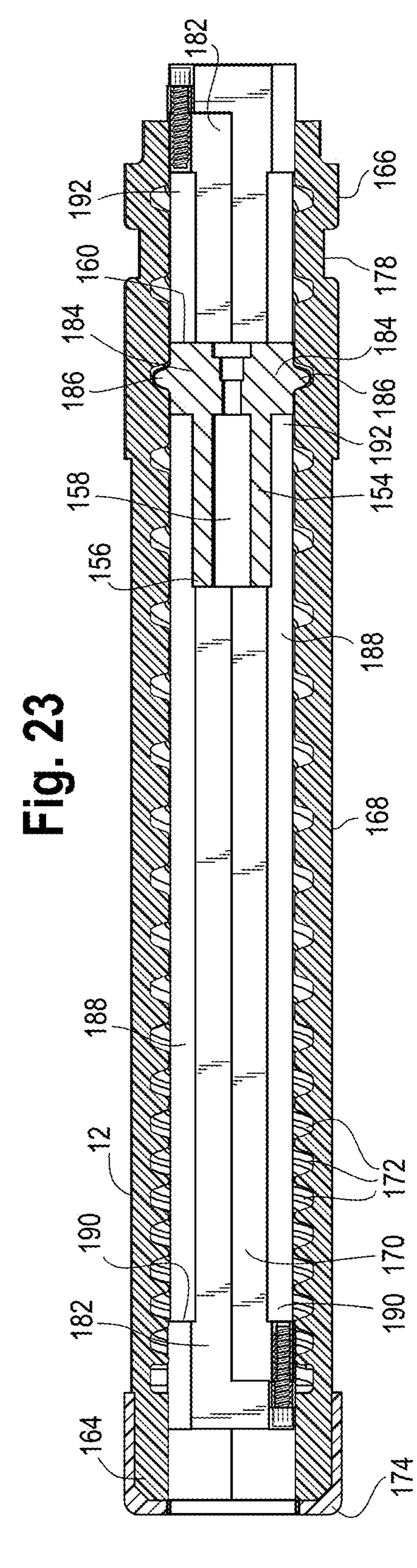
FIG. 23 is a side cross-sectional view of the front handle with the front rail and first follower disposed therein.
Figures 24, 25:
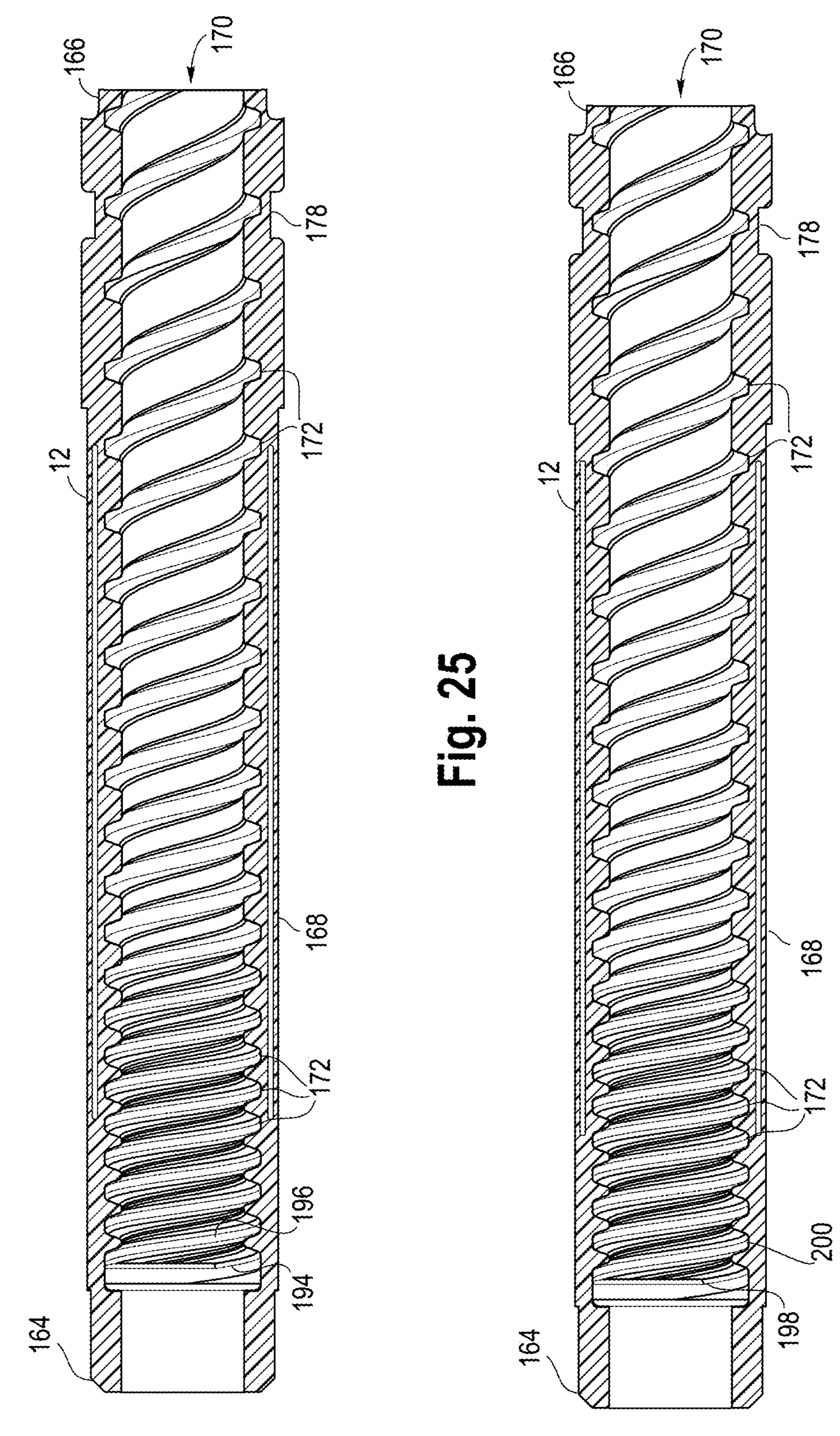
FIG. 24 is a cross-sectional view of one half of the front handle showing the dual start threads formed on the inner surface thereof.
FIG. 25 is a cross-sectional view of the other half of the front handle of FIG. 24 showing the dual start threads formed on the inner surface thereof.

As previously noted, the main handle 10 is fixed or stationary, while the front handle 12 is rotatable relative to the main handle 10. As shown in FIGS. 22 and 23, the front handle 12 has a proximal end 164 and a distal end 166 and an outer surface 168 extending there between to form a front handle interior 170. The front handle may be provided in various lengths to accommodate varying sheath pull-back or retraction requirements, depending on, for example, the particular stent graft being deployed and the procedure being performed. In one example, the longitudinal length of the front handle may be in the range of about 5 cm to about 40 cm. The front handle 12 may be constructed or molded from various materials, including, for example, acrylonitrile butadiene styrene (ABS) or a similar thermoset plastic, polymers, metals, including aluminum or stainless steel and composites (i.e., carbon, fiberglass). As shown in FIGS. 23, 24 and 25, the front handle 12 may be molded in two separate halves which are then secured together such as by welding, bonding and/or adhesives to form the front handle 12 having a threaded internal surface 172. In one example, an end cap 174 may be provided that may be fitted around and about the proximal end 164 of the front handle 12 to securely retain the separate halves of the front handle 12 together, if desired. At least a portion of the outer surface 168 of the front handle 12 may include a gripping portion for a physician to grip with one hand while manipulating the front handle 12. The gripping portion 176 of the front handle 12 is preferably ergonomically shaped for user comfort, and may be covered in a layer of softer plastic or rubber or have a gripping surface to ensure a stable grip.

The distal end 166 of the front handle 12 may include a channel 178 that extends circumferentially around the outer surface 168, while an inner surface of the main handle 10 comprises a correspondingly shaped collar 180 or one or more protrusions that extend radially inwardly from the inner surface of the main handle 10 at a location just distal of the proximal end of the main handle 10. The protrusions or collar 180 can be received by the circumferential channel 178 formed in the front handle 12 as shown in FIG. 3. The engagement between the channel 178 formed in the distal end 166 of the front handle 12 and the collar 180 extending radially inwardly from the inner surface of the main handle 10 allows for the front handle 12 to rotate with respect to the main handle 10, yet prevents the front handle 12 from sliding longitudinally (either proximally or distally) with respect to the main handle 10. Other mechanisms which allow for rotation of the front handle 12 but which prevent longitudinal movement or sliding relative to the main handle 10 may also be used as one of skill in the art would appreciate.

As shown generally in FIGS. 23 and 26-28, a front rail 182 is disposed within the front handle 12 and the first follower 154 is slideably disposed within the front rail 182. The sheath 150 may be withdrawn back or distally by rotating the front handle 12 relative to the main handle 10. As a threaded internal surface 172 of the front handle 12 engages one or more protrusions 186 extending radially outwardly from the first follower 154 and the rail 182 within the front handle 12 rotationally restrains or prevents the first follower 154 from rotating within the front rail 182. Thus, rotation of the front handle 12 pulls the first follower 154 back or distally within the front handle 12 thereby simultaneously withdrawing or retracting the sheath 150 distally to expose at least a portion of the stent graft 52. Interaction between the front handle 12, the first follower 154 and the front rail 182 to facilitate retraction of the sheath 150 will be described in further detail below.

More particularly, as shown in FIGS. 18, 19 and 23, the distal end 160 of the first follower 154 comprises at least one, and preferably two opposing ears or wings 184 extending from the outer surface of the first follower 154. A raised surface or protrusion 186 extends even further radially outwardly from each of the respective wings 184. Each of the wings 184 are shown as having a generally rectangular shape, each of which extend into and through two spaced apart longitudinal slots 188 formed in the front rail 182. If, however, the first follower 154 only had a single wing 184, then the front rail 182 may only have one slot 188 to accommodate the single wing 184.

The longitudinal slot(s) 188 formed in the front rail 182 each comprise a proximal end 190 and a distal end 192, and during sheath retraction, the first follower 154 will move or slide longitudinally from a proximal to distal direction within the front rail 182 while the wings 184 slide from the proximal end 190 of the longitudinal slot 188 to the distal end 192 of the slot. Thus, the front rail 182 allows the first follower 154 to slide longitudinally therein, while preventing rotation of the first follower. While the wings 184 are shown as having a generally rectangular shape and the longitudinal slots 188 formed in the front rail 182 are shown in FIGS. 26-28 as having a generally corresponding elongated rectangular shape for receiving the wings 184 therein, it will be appreciated that the wings 184 and the longitudinal slots 188 may be of a variety of corresponding shapes so that the wings 184 can be received within and slide along the longitudinal slot 188 formed in the front rail 182 to prevent rotation of the first follower 154 yet allowing the first follower 154 to move longitudinally within the front rail 182 while simultaneously retracting the sheath 150.

As shown in FIGS. 23 and 28, each of the respective protrusions 186 extending radially outwardly from the wings 184 are shown as having a generally conical, domed or rounded trapezoidal shape. The domed trapezoidal shape of the protrusions 186 are preferably received within and engage with threads 172 formed on the inner surface of the front handle 12. Thus, the threads 172 on the inner surface of the front handle 12 may have a correspondingly shaped conical, domed or trapezoidal configuration which receives the protrusions 186 extending radially outwardly from the first follower 154. While the protrusions 186 and the threads 172 may be formed in other shapes or configurations, it is desirable that the respective shapes of the protrusions 186 on the first follower 154 and the threads 172 formed on the inner surface of the front handle 12 can operatively engage smoothly and with minimal friction, thus allowing for ease of rotation of the front handle 12 regardless of whether the pitch of the threads 172 on the inner surface of the front handle 12 is constant or whether the pitch of the threads 172 changes or is otherwise varied.

In one example, the threads 172 on the internal surface of the front handle 12 may have a constant pitch along the longitudinal length of front handle 12, so that a particular rotation (or rotations) of the front handle 12 relative to the main handle 10 will result in a consistent longitudinal displacement or movement of the first follower 154 within the front rail 182, regardless of the position of the first follower 154 within the front rail 182. In one example, when referring to the thread pitch herein, the thread pitch is the distance between threads expressed in a particular unit of measure (mm, cm, for example) measured along a particular length, such as the length of the front handle 12. For example a thread pitch of 1.5 means that the distance between one thread 172 and the next adjacent thread 172 formed on the inner surface of the front handle 12 is 1.5 mm.

If the front handle 12 comprises threads 172 having a constant pitch, this pitch may be in the range of a pitch of about 1 mm to about 40 mm and more preferably a pitch in the range of about 5 mm to about 20 mm. The internal surface of the front handle 12 may have one thread with a single lead or point of origination, or alternatively, the inner surface of the front handle 12 may include multiple-lead threads (sometimes referred to as "dual start threads" where two or more points of origination for two or more helical thread elements corresponds to each point of origination). As shown in FIGS. 24 and 25, the front handle 12 is split into two halves, with the half shown in FIG. 24 having a first lead 194 for a first thread profile 196 and the second half shown in FIG. 25 having a second lead 198 spaced 180 degrees offset from the first lead 194 for a second thread profile 200. Multiple-lead threads allow multiple protrusions 186 extending radially outwardly from the first follower 154 to engage the respective multiple threads, thereby increasing the engaging surfaces between the first follower 154 and the threaded internal surface 172 of the front handle 12 to reduce internal forces and which allows force to be distributed equally above and below the acting longitudinal axis of the delivery system which makes a comfortable rotational actuation of the handle by the user and converts it to a high force liner motion to facilitate sheath retraction.

In another example and in contrast to the constant-pitch threads described above, the handle assembly 8 may comprise a front handle 12 having variable pitch threads 172 formed on the inner surface thereof. As shown in FIGS. 23-25, the threads 172 formed on the inner surface of the proximal end 164 of the front handle 12 may have a relatively small pitch. In one example, the pitch of the threads 172 near the proximal end 164 of the front handle 12 may be in the range of about 10 mm to about 20 mm. With relatively smaller pitch threads, each rotation of the front handle 12 may serve to retract the sheath 150 distally a relatively small longitudinal distance thus allowing the proximal end of the stent graft 52 to be exposed and deployed very gradually during the initial phases of deployment to ensure accurate positioning of the stent graft 52 within a patient's vessel. The threads 172 formed on the inner surface of the distal end 166 of the front handle 12 have a relatively greater pitch than the threads at the proximal end 164 of the front handle 12. The pitch of the distal threads will generally have a pitch of between about 1 mm and about 40 mm. As shown in FIGS. 24 and 25, the pitch of the threads 172 on the inner surface 170 of the front handle 12 generally increase from the proximal end 164 of the front handle 12 to the distal end 166 of the front handle 12, thus providing a relatively greater mechanical advantage between the rotating front handle 12 and the sheath 150. In other words, the front handle 12 facilitates a large amount of force to be exerted on to the sheath 150 with little required force by the user. Targeted variation in thread pitch along the handle 12 allows for large amounts of force and shorter longitudinal travel distance to be applied at a controllable rate for each rotation of the front handle 12 where required due to the tortuous anatomy or high device packing density while also maintaining a reasonable operating time by transitioning to a larger pitch for lower force and a longer longitudinal travel distance for each rotation of the front handle 12 as the first follower 154 engages with the threads 172 at the distal end 166 of the front handle 12. The pitch of the threads 172 may increase gradually, may increase stepwise, or may change or increase in any other incremental or pre-determined distance from a proximal to distal direction.

More specifically, the relatively smaller pitch of the threads 172 near the proximal end 164 of the front handle 12 may result in distal longitudinal movement or retraction of the sheath 150 of about 1 cm to about 10 cm per each rotation of the front handle 12, whereas the relatively greater pitch of the threads 172 near the distal end 166 of the front handle 12 may result in distal longitudinal movement or retraction of the sheath 150 of about 5 cm to about 40 cm per each rotation of the front handle 12. Thus, the variable pitch threads may provide various advantages. In one non-limiting example, after the proximal end of a stent graft 52 has been deployed within the vessel lumen and proper positioning verified by the physician, it may be desirable to proceed with deployment of the distal end of the stent graft 52 more quickly. Thus, increasing the pitch of the threads 172 near the distal end 166 of the front handle 12 allows the physician to retract the sheath 150 distally more quickly and with fewer rotations of the front handle 12 (as distal longitudinal movement of the first follower 154 within the front rail 182, which pulls the sheath 150 distally along with it) increases as the pitch of the threads 172 formed on the internal surface 170 of the front handle 12 increases) thus completing deployment of the distal end of the stent graft 52 more quickly with each rotation of the front handle 12 as compared to the distal longitudinal movement of the sheath 150 that results from each rotation of the front handle 12 during the initial stages of sheath retraction.

As shown in FIG. 22, it is preferable that the front handle 12 be rotated in only one direction to facilitate sheath retraction. As FIG. 22 shows, the front handle 12 may be rotated in a clockwise direction to cause the first follower 154 to move longitudinally within the front rail 182 to cause sheath retraction, but the modular handle assembly 8 may be manufactured and assembled in other configurations so that rotation of the front handle 12 may proceed in a counter-clockwise direction if necessary or desired. Uni-directional rotation of the front handle 12 may be ensured by a ratcheting mechanism 202 as shown in FIGS. 2 and 22. The ratcheting mechanism 202 provides for "one-way" rotation of the front handle 12 during the deployment of the prosthesis.

Specifically, as shown in FIGS. 2, 3 and 22, the ratchet mechanism 202 that ensures one-way rotation of the front handle 12 comprises, in one example, a ratchet ring 204 that is seated within the main handle 10 just distal to the distal end 166 of the front handle 12. The ratchet ring 204 comprises a set of ratcheting teeth 206 that extend proximally from the ring 204. The ratcheting teeth 206 are engaged with a corresponding set of ratcheting teeth 208 formed on the distal end 166 of the front handle 12. One or more protrusions 210 extending radially outwardly from the ratcheting ring 204 are received within correspondingly shaped channels 212 (FIG. 3) formed on the inner surface of the main handle 10, thus preventing inadvertent rotation of the ratcheting ring 204 during rotation of the front handle 12. At least one, and preferably two springs 214 are also positioned within the respective channels 212 formed on the inner surface of the main handle 10. The springs 214 push proximally and up against the protrusions 210 extending from the ratcheting ring 204, thus urging the ratchet ring 204 forward or proximally within the main handle 10, to ensure engagement between the ratcheting teeth 206 on ring 204 and the ratcheting teeth 208 formed in the distal end 166 of the front handle 12. The shape and angle of the ratcheting teeth 206 extending proximally from the ratcheting ring 204 and the correspondingly shaped ratcheting teeth 208 formed on the distal end 166 of the front handle 12 permit rotation of the front handle 12 in a first direction while restraining or otherwise preventing a second direction of front handle rotation, opposite to the first direction. In this way, rotation of the front handle 12 can only proceed in one direction (e.g. clockwise as shown in FIG. 22), thus also preventing unintended counter-rotation of the front handle 12 during sheath retraction (such as that may occur due to build-up of torsional forces, friction or other forces that may cause the front handle 12 to rotate on its own). Thus, the ratcheting mechanism 202 also helps to maintain the distal travel distance of the sheath 150 after each rotation of the front handle 12 while reducing or eliminating recoil or unintended proximal migration of the sheath 150 if/when the user releases their grip or re-grips the front handle 12 during sheath retraction. While the ratcheting mechanism 202 for ensuring uni-directional rotation of the front handle 12 has been described in one non-limiting example as a ratcheting ring 204 that is operatively engaged with ratcheting teeth

208 formed in the distal end 166 of the front handle 12, other mechanisms may be used in place of, or in combination with the above-described ratcheting mechanism 202 to ensure uni-directional rotation of the front handle 12 as would be appreciated by one of skill in the art.

As shown in FIG. 14, the main handle 10 comprises a proximal end 216 and a distal end 218 with an outer surface or side wall 220 extending there between to form a handle interior 222. As will be described below, the main handle interior 222 houses additional mechanical components that make up the handle assembly 8. The main handle 10 may be injection molded as a single unitary structure or alternatively, as shown in FIG. 10, the main handle 10 may comprise upper and lower parts or first and second halves that clam shell, lock, snap-fit or are otherwise securable to each other. The main handle 10 may be constructed of various materials including, but not limited to, acrylonitrile butadiene styrene (ABS) or a similar thermoset plastic, polymers, metals (aluminum, stainless steel) and/or composites (carbon, fiberglass) for example. As shown in FIGS. 2 and 14, the proximal end 216 of the main handle 10 includes threads 224 on the outer surface thereof. When the first and second halves of the main handle 10 are fitted together to form the main handle 10, a proximal cap 226 having internal threads on the inner surface thereof can be fitted over and about the proximal end 216 of the main handle 10 to secure the respective first and second halves of the main handle 10 together. The proximal cap 226 may also serve to support the front rotating handle 12 in position at the proximal end 216 of the main handle 10. In one example shown in FIG. 2, an end cap 228 may additionally be provided that may be fitted around and about the distal end 218 of the main handle 10 to securely retain the separate halves of the main handle 10 together, if desired.

At least a portion of the outer surface 220 of the main handle 10 may include a gripping portion 230 for a physician to grip with one hand while manipulating the front handle 12 and or rear handle 14 (such as during sheath retraction with front handle 12 or during top cap removal with rear handle 14 during stent graft deployment). The gripping portion 230 of the main handle 10 is preferably ergonomically shaped for user comfort, and may be covered in a layer of softer plastic or rubber or have a gripping surface to ensure a stable grip. As shown in FIG. 14, the gripping portion 230 may be distal to the two angled openings 232 formed generally in a center portion of the main handle 10, which openings 232 may accommodate one or more of the first side port and/or second side ports 40, 42 which extend radially outwardly from the valve 34.

As shown in FIGS. 2 and 11, located just proximally of the angled openings 232 are a series of ratcheting teeth 234 formed on the outer surface 220 of the main handle 10 and which extend at least partially circumferentially around the outer surface of the main handle 10. The ratcheting teeth 234 formed on the outer surface of the main handle 10 point in a proximal direction and are configured to engage in a correspondingly shaped set of distally facing ratcheting teeth 238 formed in a distal ratchet ring 236 that is positioned underneath and within the second or distal rotatable ring 130. The distal ratchet ring 236 may be integrally formed with the inner surface of the second rotatable ring 130 or, alternatively, the distal ratchet ring 236 may be a separately formed component which is received within the inner surface of the second rotatable ring 130 or otherwise secured (such as by adhesives, welding or other attachment mechanisms) to the inner surface of the second rotatable ring 130. For example, as shown in FIG. 2, the distal ratchet ring 236 has proximally facing extensions or arms 240 which are received within one or more recesses 242 formed in the inner surface of the second rotatable ring 130. Thus, the distal ratchet ring 236 is a separately formed component from the second rotatable ring 130, yet the distal ratchet ring 236 rotates along with the second rotatable ring 130 and ensures uni-directional rotation of the second rotatable ring 130 in a first direction while preventing the second rotatable ring 130 from rotating in a direction opposite to the first direction.

More specifically, the ratcheting teeth 238 on the distal ratchet ring 236 engage the ratcheting teeth 234 formed on the outer surface of the main handle 10 to ensure that the second rotatable ring 130 rotates in only one direction (such as clockwise, for example) while preventing counter-clockwise rotation of the second rotatable ring 130. One or more springs 237 are seated within the channels 212 formed on the inner surface of the main handle 10 and push the teeth 238 on ratchet ring 236 into engagement with the teeth 234 formed on the outer surface of the main handle 10. As such, unintended counter-rotation of the second rotatable ring 130 will be prevented. Thus, when the second rotatable ring 130 is rotated by the user, such as during retraction of one or more proximal or distal trigger wires, diameter reducing ties or other stent graft retention mechanisms, the rotation of the second rotatable ring 130 (and thus the progress of the simultaneous retraction of the trigger wires, ties, etc.) is maintained.

Similarly, as shown in FIGS. 2 and 11, the distal end of the proximal cap 226 comprises a set of ratcheting teeth 244 which extend at least partially circumferentially around the distal end of the proximal cap 226 and which point in a distal direction. The ratcheting teeth 244 which extend distally from the proximal cap 226 are configured to engage in a correspondingly shaped set of proximally facing ratcheting teeth 248 formed in a proximal ratchet ring 246 that is positioned underneath and within the first rotatable ring 128. The proximal ratchet ring 246 may be integrally formed with the inner surface of the first rotatable ring 128 or, alternatively, the proximal ratchet ring 246 may be a separately formed component which is received within the inner surface of the first rotatable ring 128 or otherwise secured (such as by adhesives, welding or other attachment mechanisms) to the inner surface of the first rotatable ring 128. For example, as shown in FIGS. 2 and 11, the proximal ratchet ring 246 has distally facing extensions or arms 250 which are received within one or more recesses 252 formed in the inner surface of the first rotatable ring 128. Thus, in this example, the proximal ratchet ring 246 is a separately formed component from the first rotatable ring 128, yet the proximal ratchet ring 246 rotates along with the first rotatable ring 128 and ensures uni-directional rotation of the first rotatable ring 128 in a first direction while preventing the first rotatable ring 128 from rotating in a direction opposite to the first direction.

More specifically, the ratcheting teeth 248 on the proximal ratchet ring 246 engage the ratcheting teeth 244 formed on the distal end of the proximal cap 226 to ensure that the first rotatable ring 128 rotates in only one direction (such as clockwise, for example) while preventing counter-clockwise rotation of the first rotatable ring 128. One or more springs 237 are seated within the one or more channels 212 formed in the inner surface of the main handle 10 to urge the teeth 248 of ratchet ring 246 into engagement with the teeth 244 formed on the distal end of the proximal cap 226. As such, unintended counter-rotation of the first rotatable ring 128 will be prevented. Thus, when the first rotatable ring 128 is rotated by the user, such as during retraction of one or more proximal and/or distal trigger wires 116, 122, 138, diameter reducing ties or other stent graft retention mechanisms, the rotation of the first rotatable ring 128 (and thus the progress of the simultaneous retraction of the trigger wires, ties, etc.) is maintained.

It can be seen in FIGS. 2 and 10-13, that the first rotatable ring 128 is a separately formed component from the second rotatable ring 130 and the first and second rotatable rings 128, 130 can rotate separately and independently from each other. As such, separate ratcheting mechanisms, such as the proximal ratcheting ring 246 ensures uni-directional rotation of the first rotatable ring 128 while the distal ratcheting ring 236 ensures uni-directional rotation of the second rotatable ring 130.

As mentioned previously, the first rotatable ring 128 is positioned just proximal to the second rotatable ring 130 about the outer surface of the main handle 10 and can be independently rotated about the main handle 10 during retraction and removal of one or more trigger wires, diameter reducing ties or other stent graft retention mechanisms during a stent graft deployment procedure. As shown in FIG. 2 and FIG. 11, the main handle 10 comprises one or more grooves or threads 224 formed in the outer surface thereof at a location which is generally disposed under the first and second rotatable rings 128, 130. For example, the main handle 10 may comprise a set of proximal threads 254 and a set of distal threads 256. In one example, the proximal threads 254 may be formed as a groove in the outer surface of the main handle 10 which wraps around the outer surface of the main handle 10 in a counter-clockwise direction. The point of origination 258 of the proximal threads 254 is longitudinally spaced from the point of termination 260 of the proximal threads 254, with, in the example shown, the points of origination 258 and termination 260 longitudinally separated by two threads. The point of termination 260 of the proximal threads 254 includes an opening or aperture 134 formed in the main handle 10, thus providing an opening through which one or more of the proximal trigger wires 116, 122, distal trigger wires 138 and/or diameter reducing ties can pass, allowing the wires and/or ties to extend from the inner surface of the first rotatable ring 128, through the opening 134 formed at the point of termination 260 of the proximal threads 254 and into the centrally located port 44 in valve 34 located within the main handle 10, from which point the wires and/or ties extend proximally through the positioner 30 to the stent graft 52.

During a procedure, the user may rotate the first rotatable ring 128 (such as in a clockwise direction as shown in FIG. 13) which causes any one or more of the trigger wires and/or diameter reducing ties which are secured to the inner surface of the first rotatable ring 128 to begin wrapping within the proximal threads 254, as the wires and/or ties are retracted from the stent graft 52. In one non-limiting example, the proximal trigger wires 116, 122 may be secured to the inner surface of the first rotatable ring 128, such as by a set screw, adhesives, or other attachment mechanisms, thus, as the user rotates the first rotatable ring 128, the proximal trigger wires 116, 122 begin to wrap around the outer surface of the main handle 10 within the helical groove provided by the proximal threads 254 as shown in FIG. 13. As the first rotatable ring 128 continues to be rotated by the user, the proximal trigger wires 116, 122 continue to follow the helical pathway and wrap within the proximal threads 254 until the proximal trigger wires 116, 122 are released from the proximal end of the stent graft 52. As such, tension in the wires is maintained while allowing the wires to remain "hidden" during retraction to eliminate the possibility of entanglement with each other or with other parts of the device or other surgical tools being used. The helical groove provided by the proximal threads 254 may be a pre-determined length that may be slightly longer than the required actuation length for the particular trigger wire(s) being retracted, thereby providing a positive mechanical stop as an indication to the user when the retraction of one or both of the proximal trigger wires 116, 122 is complete.

The user may continue to rotate the first rotatable ring 128 until the proximal trigger wires 116, 122 have fully wrapped around the outer surface of the main handle 10 within the proximal threads 254, thereby maintaining the now-retracted proximal trigger wires 116, 122 seated in position within the proximal threads 254 to prevent the proximal trigger wires 116, 122 from tangling or catching on other portions of the device or interfering with subsequent steps of deployment. In other words, the proximal threads 254 provide a storage or holding place for the proximal trigger wires 116, 122 during retraction as well as after they have been retracted and the proximal end of the stent graft 52 released.

Although rotation of the first rotatable ring 128 is described above as facilitating retraction of the proximal trigger wires 116, 122, it is also contemplated that both the proximal and distal trigger wires 116, 122, 138 may be secured to the inner surface of the first rotatable ring 128 such that rotation of the first rotatable ring 128 causes both the proximal and distal trigger wires 116, 122, 138 to wrap within the proximal threads 254 and remain there while the proximal and distal ends of the stent graft 52 are released.

Similarly, as shown in FIGS. 11 and 12, the set of distal threads 256 may be formed as a groove in the outer surface of the main handle 10 which wraps around the outer surface of the main handle 10 in a counter-clockwise direction. In the example shown, the set of distal threads 256 are a mirror-image of the set of proximal threads 254 which may allow for both the first rotatable ring 128 and the second rotatable ring 130 in the same direction. The point of origination 262 of the distal threads 256 is longitudinally spaced from the point of termination 264 of the distal threads 256, with, in the example shown, the points of origination 262 and termination 264 longitudinally separated by two threads. The point of termination 264 of the distal threads 256 includes an opening or aperture 136 formed in the main handle 10, thus providing an opening through which one or more of the proximal trigger wires 116, 122, distal trigger wires 138 and/or diameter reducing ties can pass, allowing the wires and/or ties to extend from the inner surface of the second rotatable ring 130, through the opening 136 formed at the point of termination 264 of the distal threads 256 and into the centrally located port 44 in valve 34 within the main handle 10, from which point the wires and/or ties extend proximally through the positioner 30 to the stent graft 52.

During a procedure, the user may rotate the second rotatable ring 130 (such as in a clockwise direction) which causes any one or more of the trigger wires and/or diameter reducing ties which are secured to the inner surface of the second rotatable ring 130 to begin wrapping within the distal threads 256, as the wires and/or ties are retracted from the stent graft 52. In one non-limiting example, the distal trigger wires 138 and any additional diameter reducing ties may be secured to the inner surface of the second rotatable ring 130, such as by a set screw, adhesives, or other attachment mechanisms. Thus, as the user rotates the second rotatable ring 130, the distal trigger wires 138 (and/or any other diameter reducing ties) begin to wrap around the outer surface of the main handle 10 within the helical groove provided by the distal threads 256. As the second rotatable ring 130 continues to be rotated by the user, the distal trigger wires 138 (and/or any other diameter reducing ties) continue to wrap within the distal threads 256 until the distal trigger wires 138 (and/or ties) are released from the stent graft. As such, tension in the wires 138 is maintained while allowing the wires to remain "hidden" during retraction to eliminate the possibility of entanglement with other parts of the device or other surgical tools being used. The helical groove provided by the distal threads 256 may be a pre-determined length that may be slightly longer than the required actuation length for the particular trigger wire(s) being retracted, thereby providing a positive mechanical stop as an indication to the user when the retraction of one or both of the proximal trigger wires 138 is complete.

The user may continue to rotate the second rotatable ring 130 until the distal trigger wires 138 and/or any other diameter reducing ties have fully wrapped around the outer surface of the main handle 10 within the distal threads 256, thereby maintaining the now-retracted distal trigger wires 138 and/or additional ties seated in position within the distal threads 256 to prevent the distal trigger wires 138 or any other diameter reducing ties from tangling or catching on other portions of the device or interfering with subsequent steps of deployment. In other words, the distal threads 256 provide a storage or holding place for the distal trigger wires 138 and/or any other diameter reducing ties during retraction and after they have been retracted and the stent graft released. Thus, like the first rotatable ring 128, the second rotatable ring 130 also contains all parts associated with trigger wire retraction, including the trigger wires 116, 122 and 138 themselves during and after actuation, while hiding the wires when retraction is complete.

Although rotation of the first rotatable ring 128 is described above as facilitating retraction of the proximal trigger wires 116, 122, it is also contemplated that both the proximal and distal trigger wires 116, 122, 138 and/or any other diameter reducing ties may be secured to the inner surface of the first rotatable ring 128 such that rotation of the first rotatable ring 128 causes both the proximal and distal trigger wires 116, 122, 138 (and/or other diameter reducing ties) to wrap within the proximal threads 254 and remain there as the proximal and distal ends of the stent graft 52 are released. Likewise, the second rotatable ring 130 may facilitate retraction of proximal and distal trigger wires 116, 122, 138 and/or any other diameter reducing ties. In other words, both the first rotatable ring 128 and the second rotatable ring 130 may be used to facilitate retraction and release of any one or more trigger wires, diameter reducing ties or combinations thereof. The function of the particular rotatable ring (either the first rotatable ring 128 or the second rotatable ring 130) may be determined by which of the trigger wires or diameter reducing ties are secured to its inner surface, such that when the first rotatable ring 128 or the second rotatable ring 130 is rotated by the user, the particular trigger wire(s) or diameter reducing tie(s) which are attached to that particular rotatable ring will be retracted while the remaining trigger wire(s) or diameter reducing tie(s) would be retracted by separate and independent rotation of the other of the two rotatable rings during deployment.

Also, although the proximal and distal threads 254, 256 are described above as being wrapped in a particular direction, either clockwise or counter-clockwise and having points of origination and points of termination at a specific location and being longitudinally spaced by a particular number of threads, it will be appreciated that the proximal and distal threads 254, 256 can be helically wound in any direction about the outer surface of the main handle 10 and can comprise any number of threads (e.g. more or fewer threads than shown in the Figures and described above, with points of origination and termination formed in any location on the main handle 10 and separated by any number of threads as necessary or desired.

Figures 32, 33:
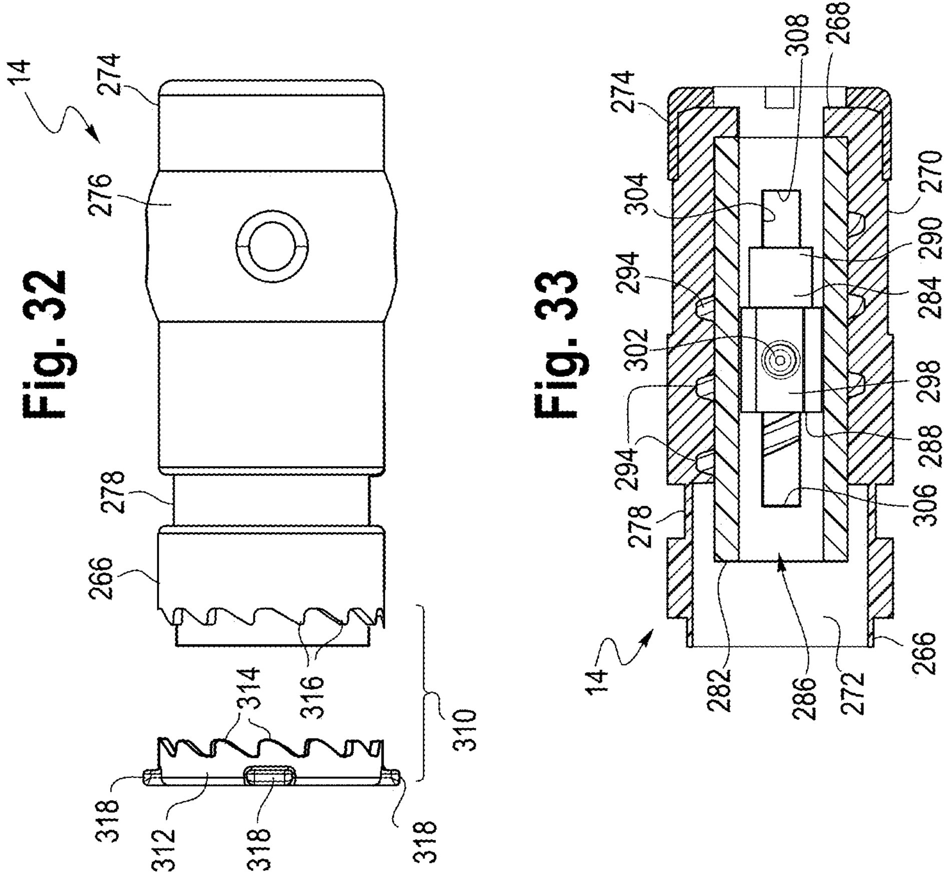
FIG. 32 is a side view of the rear handle and ratcheting mechanism.
FIG. 33 is a side cross-sectional view of the rear handle with the rear rail and second follower disposed therein.

As shown in FIGS. 1-3, extending distally from the main handle 10 is rear handle 14. The rear handle 14 has a proximal end 266, a distal end 268, and an outer wall 270 extending there between, thus forming a rear handle interior 272 as shown in FIGS. 32 and 33. The rear handle 14 is rotatable relative to the main handle 10. Like the front handle 12, the rear handle 14 may be injection molded as a single unitary structure or alternatively, as shown in FIG. 33, the rear handle 14 may comprise upper and lower parts or halves that clam shell, lock, snap-fit or are otherwise securable to each other. The rear handle may be constructed of a variety of materials, including but not limited to acrylonitrile butadiene styrene (ABS) or a similar thermoset plastic, polymers, metals (aluminum, stainless steel) and composites (carbon, fiberglass). In one example, an end cap 274 may be provided that may be fitted around and about the distal end 268 of the rear handle 14 to securely retain the separate halves of the rear handle 14 together, if desired. At least a portion of the outer surface 270 of the rear handle 14 may include a gripping portion 276 for a physician to grip with one hand while manipulating the rear handle 14. The gripping portion 276 of the rear handle 14 is preferably ergonomically shaped for user comfort, and may be covered in a layer of softer plastic or rubber or have a gripping surface to ensure a stable grip.

The proximal end 266 of the rear handle 14 may include a channel 278 that extends circumferentially around the outer surface 270 near the proximal end 266 of the rear handle 14, while the inner surface of the main handle 10 comprises a correspondingly shaped collar 280 or one or more protrusions that extend radially inwardly from the inner surface of the main handle 10 at a location just proximal of the distal end 218 of the main handle 10. The protrusions or collar 280 can be received by the circumferential channel 278 formed in the rear handle 14. The engagement between the channel 278 formed in the rear handle 14 and the collar 280 extending radially inwardly from the inner surface of the main handle 10 allow for the rear handle 14 to rotate with respect to the main handle 10, yet prevent the rear handle 14 from sliding longitudinally (either proximally or distally) with respect to the main handle 10. Other mechanisms which allow for rotation of the rear handle 14 but which prevent longitudinal movement or sliding relative to the main handle 10 may also be used as one of skill in the art would appreciate. Further, the size, shape and configuration of the channel 278 and collar 280 are preferably the same as or similar to the size, shape and configuration of the channel 178 formed in the distal end 166 of the front handle 12 and the correspondingly shaped collar 180 formed on the inner surface of the main handle 10. As such, the standardization between these respective engaging surfaces would allow the position of the front handle 12 and the rear handle 14 to be reversed or interchanged with respect to the main handle as shown in FIG. 4 and described in further detail below.

As shown generally in FIGS. 29-31 and 33, a rear rail 282 is disposed within the rear handle 14 and a second follower 284 is slideably disposed within the rear rail 282. With reference to FIGS. 20 and 21, the inner cannula 22 extends longitudinally through the lumen 286 of the second follower 284. The lumen 286 of the second follower 284 may have a larger internal diameter at a distal end 290 of the second follower and a relatively smaller internal diameter at a proximal end 288 of the second follower 284. The pin vice 24 is secured to the distal end of the inner cannula 22 and the pin vice 24 may be coupled or secured to the second follower 284, thus securing the second follower 284 to the distal end of the inner cannula 22, although other suitable mechanisms for attaching the inner cannula 22 to the second follower 284 are also contemplated, including adhesives, welding and the like. In one example shown in FIG. 20, the proximal end 292 of the pin vice 24 has external threads which may mate with and engage with internal threads 294 formed on the inner surface of the distal end 290 of the second follower 284, thus securing the pin vice 24, the inner cannula 22 and the second follower 284 to each other. As such, when the second follower 284 is moved longitudinally within the rear rail 282, the inner cannula 22 is also moved longitudinally.

Figure 35:
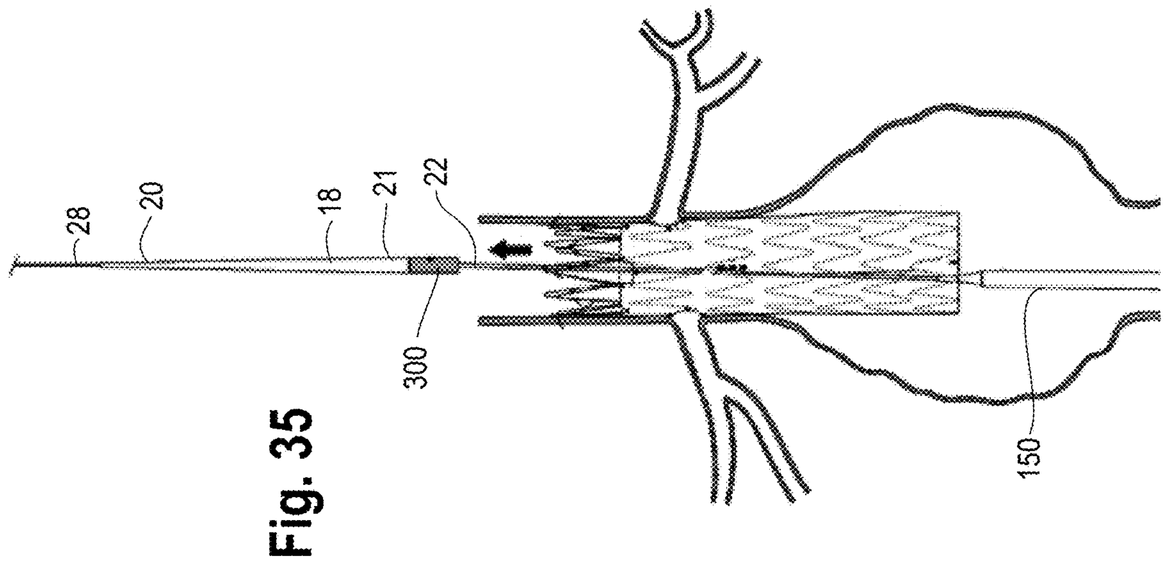
FIG. 35 illustrates the inner cannula, nose cone and top cap pushed proximally to deploy the proximal stent within a vessel.
Figure 34:
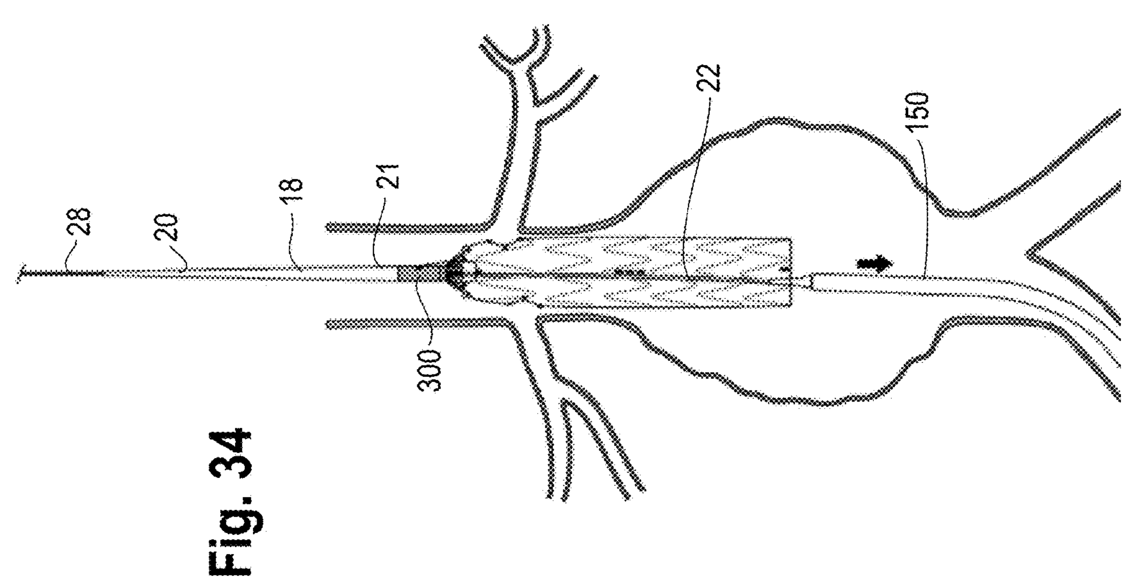
FIG. 34 illustrates one example of the delivery device within a patient's vasculature and the proximal end of a stent graft retained by a top cap.

The inner cannula 22 may be pushed forward or proximally relative to the device 2 by rotating the rear handle 14 relative to the main handle 10. As a threaded internal surface 296 of the rear handle 14 engages one or more protrusions 298 extending radially outwardly from the second follower 284, the rear rail 282 within the rear handle 14 rotationally restrains or prevents the second follower 284 from rotating within the rear rail 282. Thus, rotation of the rear handle 14 pulls the second follower 284 forward or proximally within the rear rail 282 inside of the rear handle 14 thereby simultaneously pushing the inner cannula 22 forward or proximally. Pushing the inner cannula 22 in a proximal direction simultaneously causes proximal longitudinal movement of the inner cannula 22 as well as proximal movement of the nose cone 18. If a top cap 300 is present, as shown in FIGS. 34 and 35, the top cap 300 will also move proximally with the nose cone 18. As the nose cone 18 and top cap 300 are pushed proximally, the top cap 300 is lifted off of the proximal stent, thus allowing the proximal stent to fully deploy, as shown in FIG. 35 and described in further detail below.

More particularly, the proximal end 288 of the second follower 284 comprises at least one, and preferably two opposing ears or wings 298 extending from the outer surface of the second follower. A raised surface or protrusion 302 extends even further radially outwardly from each of the respective wings 298. Each of the wings 298 are shown as having a generally rectangular shape, each of which extend into and through two spaced apart longitudinal slots 304 formed in the rear rail 282, as shown in FIGS. 29-31 and 33. If, however, the second follower 284 only had a single wing, then the rear rail 282 may only have one slot 304 to accommodate the single wing.

The longitudinal slot(s) 304 formed in the rear rail 282 each comprise a proximal end 306 and a distal end 308 and during rotation of the rear handle 14 the second follower 284 will move or slide longitudinally from a distal to proximal direction within the rear rail 282 while the wings 298 slide from the distal end 308 of the slot 304 to the proximal end 306 of the slot 304. Thus, the rear rail 282 allows the second follower 284 to slide longitudinally therein, while preventing rotation of the second follower 284. While the wings 298 are shown as having a generally rectangular shape and the longitudinal slots 304 formed in the rear rail 282 are shown as having a generally corresponding elongated rectangular shape for receiving the wings 298 therein, it will be appreciated that the wings 298 and the longitudinal slots 304 may be of a variety of corresponding shapes so that the wings 298 can be received within and slide along the longitudinal slot 304 formed in the rear rail 282 to prevent rotation of the second follower 284 yet allowing the second follower to move longitudinally within the rear rail 282 while simultaneously pushing the inner cannula 22 in a proximal direction.

As shown in FIG. 31 and FIG. 33, each of the respective protrusions 302 extending radially outwardly from the wings 298 are shown as having a generally conical, domed or rounded trapezoidal shape. The domed trapezoidal shape of the protrusions 302 are preferably received within and engage with threads 296 formed on the inner surface of the rear handle 14. Thus, the threads 296 on the inner surface of the rear handle 14 may have a correspondingly shaped conical, domed or trapezoidal configuration which receives the protrusions 302 extending radially outwardly from the second follower 284. While the protrusions 302 and the threads 296 may be formed in other shapes or configurations, it is desirable that the respective shapes of the protrusions 302 on the second follower 284 and the threads 296 formed on the inner surface of the rear handle 14 can operatively engage smoothly and with minimal friction, thus allowing for ease of rotation of the rear handle 14 regardless of whether the pitch of the threads 296 on the inner surface of the rear handle 14 is constant or whether the pitch of the threads is variable or otherwise changes.

As shown in FIG. 33, the threads 296 on the internal surface of the rear handle 14 may have a constant pitch along the longitudinal length of rear handle 14, so that a particular rotation (or rotations) of the rear handle 14 relative to the main handle 10 will result in a consistent longitudinal displacement or movement of the second follower 284 within the rear rail 282, regardless of the second follower's position within the rear rail 282. If the rear handle 14 comprises threads 296 having a constant pitch, this pitch may be in the range of a pitch of about 1 mm to about 40 mm. Like the front handle 12 shown in FIGS. 24 and 25, the internal surface of the rear handle 14 may have one thread with a single lead or point of origination, or alternatively, the inner surface of the rear handle 14 may include multiple-lead threads (sometimes referred to as "dual start threads", where two or more points of origination for two or more helical thread elements corresponding to each point of origination). Multiple-lead threads allow multiple protrusions 302 extending radially outwardly from the second follower 284 to engage the respective multiple threads, thereby increasing the engaging surfaces between the second follower 284 and the threaded internal surface of the rear handle 14.

In another example and in contrast to the constant-pitch threads described above, the rear handle 14 may have variable pitch threads formed on the inner surface thereof. For example, the threads 296 formed on the inner surface of the distal end 268 of the rear handle 14 may have a relatively small pitch. With relatively smaller pitch threads, each rotation of the rear handle 14 may serve to push the inner cannula 22 proximally a relatively small longitudinal distance at first, thus also pushing any top cap 300 (if present) off of the proximal apices of a proximal stent, such as bare stent 80 of stent graft 74 shown in FIG. 8 or the proximal apices of another proximal stent shown in FIGS. 34 and 35) allowing the proximal end 76 of the exemplary stent graft 74 to be released from the top cap 300 and deployed very gradually during the initial phases of top cap removal to ensure accurate positioning of the stent graft within a patient's vessel. The threads 296 formed on the inner surface of the proximal end 266 of the rear handle 14 may have a relatively greater pitch than the threads at the distal end 268 of the rear handle 14. The pitch of the threads 296 may change gradually, and may increase step-wise, or may change or increase in any other incremental or pre-determined distance from a proximal to distal direction along the inner surface of the rear handle.

As already described in detail above, variable pitch threads may provide various advantages. In one non-limiting example, after the top cap 300 has been pushed proximally off of the proximal stent and proper positioning verified by the physician, it may be desirable to proceed with the final removal of the top cap 300 more quickly. Thus, increasing the pitch of the threads near the proximal end 266 of the rear handle 14 allows the physician to push the inner cannula 22 (and thus the top cap 300) in a proximal direction more quickly and with fewer rotations of the rear handle 14 thus completing deployment more quickly with each rotation of the rear handle 14 as the second follower 284 engages the threads 296 with the relatively greater pitch.

As shown in FIG. 32, it is preferable that the rear handle 14 be rotated in only one direction to facilitate proximal longitudinal movement of the inner cannula 22 and top cap 300 removal. In one example, the rear handle 14 may be rotated in a clockwise direction to cause the second follower 284 to move longitudinally within the rear rail 282 to cause proximal movement of the inner cannula 22, but the modular handle assembly 8 may be manufactured and assembled in other configurations so that rotation of the rear handle 14 may proceed in a counter-clockwise direction if necessary or desired. Uni-directional rotation of the rear handle 14 may be ensured by a ratcheting mechanism 310 as shown in FIGS. 2 and 32. The ratcheting mechanism 310 provides for "one-way" rotation of the rear handle 14 during the deployment of the prosthesis.

Specifically, the ratchet mechanism 310 that ensures one-way rotation of the rear handle 14 comprises, in one example, a ratchet ring 312 that is seated within the main handle 10 just proximal to the distal end 218 of the main handle 10. The ratchet ring 312 comprises a set of ratcheting teeth 314 that extend distally from the ring 312. The ratcheting teeth 314 are engaged with a corresponding set of ratcheting teeth 316 formed on the proximal end 266 of the rear handle 14. One or more protrusions 318 extending radially outwardly from the ratcheting ring 312 are received within correspondingly shaped channels 320 formed on the inner surface of the main handle 10, thus preventing inadvertent rotation of the ratcheting ring 312 during rotation of the rear handle 14. At least one, and preferably two springs 322 are also positioned within the respective channels 320 formed on the inner surface of the main handle 10. The springs 322 push distally and up against the protrusions 318 extending from the ratcheting ring 312, thus urging the ratchet ring 312 rearward or distally within the main handle 10, to ensure engagement between the ratcheting teeth 314 on ring 312 and the ratcheting teeth 316 formed in the proximal end 266 of the rear handle 14. The shape and angle of the ratcheting teeth 314 extending distally from the ratcheting ring 312 and the correspondingly shaped ratcheting teeth 316 formed on the proximal end 266 of the rear handle 14 permit rotation of the rear handle in a first direction while restraining or otherwise preventing a second direction of second handle rotation, opposite to the first direction. In this way, rotation of the rear handle 14 can only proceed in one direction (e.g. clockwise), thus also preventing unintended counter-rotation of the rear handle 14 during proximal longitudinal movement of the inner cannula 22 during removal of the top cap 300 (such as that may occur due to build-up of torsional forces, friction or other forces that may cause the rear handle 14 to rotate on its own). Thus, the ratcheting mechanism 310 also helps to maintain the proximal travel distance of the inner cannula 22 after each handle rotation while reducing or eliminating recoil or unintended distal migration of the inner cannula 22 if/when the user releases their grip or re-grips the rear handle 14 during top cap removal.

While the ratcheting mechanism 310 for ensuring uni-directional rotation of the rear handle 14 has been described in one non-limiting example as a ratcheting ring 312 that is operatively engaged with ratcheting teeth 316 formed in the proximal end 266 of the rear handle 14, other mechanisms may be used in place of, or in combination with the above-described ratcheting mechanism 310 to ensure uni-directional rotation of the rear handle 14 as would be appreciated by one of skill in the art.

In one alternative configuration of the modular handle assembly 8, as one of skill in the art would appreciate, rotation of the rear handle 14 may not always be necessary and/or desired for the delivery and deployment of certain prostheses 52 and/or during use of the device 2 in particular procedures. In one non-limiting example, if the device 2 is used to deliver a stent graft or other prosthesis 52 that does not utilize a top cap 300 to releasably constrain the proximal end of the stent graft 52, then rotation of the rear handle 14 to facilitate proximal longitudinal movement of the inner cannula 22 to remove a top cap 300 may no longer be a necessary step in a deployment sequence. For example, a stent graft 52 configured for delivery and deployment to an iliac artery, such as that shown in FIG. 7, does not include a proximal bare stent (such as bare stent 80 shown in FIG. 8) that would require restraint by a top cap 300 in the delivery device 2, thus a top cap 300 at the proximal end of the inner cannula 22 would not likely be present. In such a case, the rear handle 14 may be pre-rotated or otherwise locked during manufacture so that upon arrival to the end-user, rotation of the rear handle 14 (and thus longitudinal movement of the inner cannula 22) is prevented.

For example, during manufacture the rear handle 14 may be rotated so that the second follower 284 is moved as far to the proximal end 306 of slot 304 formed in the rear rail 282 as far as possible. Thus, even if the user tried to rotate the rear handle 14 during use, the rear handle would be prevented from rotating because the second follower 284 (which is engaged with the threads 296 formed on the inner surface of the rear handle 14) would be at the proximal-most position 306 within the rail 282, thus serving as a stop or lock and preventing the rear handle 14 from any possible further rotation. In other words, if the second follower 284 cannot move or slide further longitudinally within the rear rail 282, then rotation of the rear handle 14 cannot proceed. Rotation of the rear handle 14 in the opposite direction would also be prevented due to the ratcheting mechanism 310. As such, manipulation (rotation) of the rear handle 14 can be prevented when the delivery device 2 is intended to be used with particular prostheses that do not require proximal longitudinal motion of the inner cannula 22, including proximal longitudinal motion of the inner cannula 22 during removal of a top cap 300, for example.

In another alternative configuration, such as when the delivery device 2 is used to deliver a stent graft 52 having a side arm or fenestration (such as side arm 66 of stent graft 54 shown in FIG. 7) that must be cannulated and/or when the device 2 is used to deliver a prosthesis 52 to a vessel having a branch vessel extending from a main vessel where cannulation of the branch vessel is necessary or desired, the delivery device 2 may comprise a cannulating catheter such as catheter 50 shown in FIGS. 1, 3 and 5. In such a case, the nose cone 18 may be provided with a channel or groove 324, such as that shown in FIG. 5. The proximal end of the cannulating catheter 50 may extend through the groove 324 formed in the nose cone dilator 18 and conform to the shape and configuration of the groove 324. The cannulating catheter 50 may be held securely in the groove 324 (such as by the surrounding sheath 150) until the sheath 150 is retracted during deployment. The user may manipulate the cannulating catheter 50 at its distal end, such as where it exits side port 42, to move the cannulating catheter 50 proximally and distally and/or otherwise maneuver it in order to cannulate a branch vessel. One example of cannulating a branch vessel using a cannulating catheter is described in U.S. Provisional Application No. 62/148,006 filed on Apr. 15, 2015 and U.S. Provisional Application No. 62/164,184 filed on May 20, 2015, which applications are incorporated by reference in their entireties. However, as FIG. 5 shows, the delivery device 2 may be used to deliver various types of prostheses or stent grafts (like the exemplary prosthesis 52 shown in dashed lines in FIG. 5) illustrating that this is one of many types of stent grafts that may be releasably coupled to and deployed using the delivery device 2), and in instances in which side arm or branch vessel cannulation is not necessary or desired (e.g. such as with the stent graft shown generally in FIGS. 7 and/or 9), then the cannulating catheter 50 may be eliminated from the device 2 and the particular side port 40 and/or 42 in the valve 34 through which it would have extended may be sealed or used for other purposes.

Also, as described above and shown in exemplary FIG. 4, the modular handle assembly 8 may be assembled so that the relatively longer front handle 12 extends proximally from the main handle 10 while the relatively shorter rear handle 14 extends distally from the main handle 10. Thus, the longitudinal length of travel of the sheath 150 during sheath retraction is generally equivalent to the length of travel of the first follower 154 in the front rail 182. Likewise, the longitudinal length of proximal travel of the inner cannula 22 to push the nose cone 18 and top cap 300 proximally during deployment is generally equivalent to the distance of travel of the second follower 284 in the rear rail 282.

However, as previously mentioned, it may be advantageous, in certain circumstances and procedures and depending on the particular prosthesis being delivered by the device 2, to configure and assemble the modular handle assembly 8 differently. In one example, the positions of the relatively longer front handle 12 and the shorter rear handle 14 can be switched or reversed relative to the main handle 10, such that the longer "front" handle 12 now extends distally from the main handle 10 while the shorter "rear" handle 14 now extends proximally from the main handle 10. This alternate "reversed" configuration is shown generally in FIG. 4.

In one example, the configuration of the handle assembly 8 shown in FIG. 4 may be desirable where the stent graft 52 being delivered by the device 2 has a relatively shorter length and does not require as great of a distance of longitudinal travel during sheath retraction to expose the graft as would be provided by the relatively longer front handle 12. As such, the relatively shorter "rear" handle 14 may be positioned as the "front" handle extending proximally from the main handle 10 as FIG. 4 shows. Thus, during sheath retraction, the user would rotate the relatively shorter handle 14 (which is now serving as the "front" handle), and the distance of longitudinal sheath retraction would be substantially equivalent to the distance of travel of the second follower 284 within the rail 282 from a proximal position to a distal position within the rail 282 to expose the stent graft 52.

In another example, the configuration of the handle assembly 8 shown in FIG. 4 may be desirable if the sheath 150 covering the stent graft 52 is a "split sheath," meaning that there is a split (not shown) at a point between the proximal and distal ends of the sheath 150, resulting in a proximal sheath segment and a distal sheath segment that must both be removed to expose the stent graft 52. A split sheath may be used, in one example, to radially restrain a stent graft such as that shown in FIG. 9, which the split in the sheath generally aligned with fenestration 104 formed in the stent graft. This may allow cannulation of a branch vessel through fenestration 104 before one or both of the sheath segments are removed. Removal of the proximal sheath segment and the distal sheath segment often proceeds in two separate actions or manipulations of the handle assembly 8. The first action is to retract the distal sheath segment distally to remove it from the distal end of the stent graft 52 with the front handle, while the second action is to push the proximal segment of the sheath 150 proximally to remove it from the proximal end of the stent graft 52 with the rear handle. In such a case, the distal sheath segment may be relatively shorter than the proximal sheath segment, thus the relatively shorter handle 14 may be better suited for providing the shorter longitudinal travel distance for retraction and removal of the distal sheath segment from the distal end of the stent graft 52. Likewise, the relatively longer handle 12 may be better suited for providing the longer longitudinal travel distance for pushing the proximal sheath segment proximally to expose the proximal end of the stent graft 52. More particularly, the proximal sheath segment may be attached at its proximal end to the distal end of the nose cone 18 (the proximal sheath segment thus being indirectly attached to the inner cannula 22 via the nose cone 18). Thus, the modular handle assembly 8 may be assembled such that the relatively shorter "rear" handle 14 extends proximally from the main handle 10 (thus serving as a front handle) while the relatively longer "front" handle 12 extends distally from the main handle 10 (thus serving as a rear handle) as shown in FIG. 4. Rotation of the relatively shorter handle 14 facilitates distal retraction of the shorter distal sheath segment, while subsequent rotation of the relatively longer handle 12 facilitates proximal longitudinal movement of the inner cannula 22 and nose cone 18, thus simultaneously pushing the proximal sheath segment proximally with them to expose the proximal end of the stent graft 52 to complete deployment. Further details of a split sheath and manipulation thereof using a handle assembly 8 are described in U.S. Provisional Application No. 62/064,595 filed on Oct. 16, 2014, which is incorporated by reference herein in its entirety.

Thus, advantageously, the modular design of the handle assembly 8 facilitates the interchangeability of the front handle 12 and the rear handle 14 relative to the main handle 10 depending on the procedure being performed, the particular configuration of the prosthesis being deployed, the design of the sheath (unitary sheath or split sheath), the presence of a top cap, the presence of a cannulating cannula, as well as other factors. In other words, there is flexibility in the ways in which the various parts that make up the handle assembly 8 can be configured and assembled as desired or required by the user.

Before use of the delivery device 2 and when the delivery device is tracked to a desired location within a patient's body, the first follower 154 is disposed in a proximal-most position 190 within the front rail 182 (and if a top cap 300 is present to restrain the proximal end of the stent graft, then the second follower 284 is in the distal-most position 308 within the rear rail 282) and the stent graft 52 at the proximal end 4 of the delivery device 2 is fully covered by sheath 150 and held in a radially inwardly contracted condition. To retract the sheath 150, the front handle 12 is rotated by the user (such as in a clockwise direction) while the ratchet ring 204 prevents counter-rotation of the front handle 12. If the threads 172 formed on the inner surface of the front handle 12 are variable pitch threads, then the distance of longitudinal travel during the initial stages of sheath retraction is smaller with each handle rotation as the first follower 154 engages the smaller pitch threads, while the distance of longitudinal travel of the sheath 150 during later stages of sheath retraction with each handle rotation increases as the first follower 154 engages the larger pitch threads towards the distal end 166 of the front handle 12.

When the sheath 150 has been retracted distally a sufficient distance to expose at least the proximal end of the stent graft 52, the user may proceed with removal of at least the proximal trigger wires 116, 122 and any other diameter reducing ties that may be present at the proximal end of the stent graft 52. To release the proximal trigger wires 116, 122 and/or other diameter reducing ties, the user may rotate the first rotatable ring 128. Rotation of the first rotatable ring 128 causes the proximal trigger wires 116, 122 and/or additional proximal ties to wind around the outer surface of the main handle 10 within the proximal helical threads 254. Rotation of the first rotatable ring 128 may continue until the proximal trigger wires 116, 122 are fully wrapped within the proximal helical threads 254 and the first rotatable ring 128 can then no longer be rotated any further.

After removal of the proximal trigger wires 116, 122 and/or proximal ties have been removed from the proximal end of the stent graft 52, the user may manipulate the cannulating catheter 50, if present, to cannulate any one or more branch vessels extending from a main vessel in which the stent graft 52 is being deployed. This particular step of a deployment sequence may only be desired in instances where the stent graft 52 being deployed comprises a fenestration or side arm (such as side arm 66 of stent graft 64 shown in FIG. 7) and is configured to be deployed in a vessel where branch vessel cannulation is necessary or desired. In a non-limiting example, this particular step may be desirable for cannulation of a subclavian artery when the stent graft is being deployed in the aortic arch (such as the stent graft shown in FIG. 9) or alternatively, for cannulation of an internal iliac artery when the stent graft is being deployed in the common and/or external iliac artery (such as the stent graft shown in FIG. 7). Once a branch artery has been properly cannulated, an additional prosthesis, such as an extension graft (not shown) may be deployed over and/or through the pathway into the branch artery provided by the cannulating cannula 50. This extension graft may extend from one or more fenestrations or side arms formed in the stent graft, such as the side arm 66 shown in FIG. 7 or side arm 108 shown in FIG. 9.

At this time, the user may retract the sheath 150 further to expose the main body and/or the distal end of the stent graft 52 if this was not already done with the first stage of sheath retraction described above. When the sheath 150 has been sufficiently retracted to expose the distal end of the stent graft, the user may then rotate the second rotatable ring 130 to retract the distal trigger wires 138 and/or any other diameter reducing ties that may be present. Rotation of the second rotatable ring 130 causes the distal trigger wires 138 and/or additional distal ties to wind around the outer surface of the main handle 10 within the distal helical threads 256. Rotation of the second rotatable ring 130 may continue until the distal trigger wires 138 are fully wrapped within the distal helical threads 256 and the second rotatable ring 130 can then no longer be rotated any further.

In this particular example of a method of use, rotation of the first rotatable ring 128 facilitates retraction of the proximal trigger wires 116, 122 and any other proximal diameter reducing ties (if present), while rotation of the second rotatable ring 130 facilitates retraction of the distal trigger wires 138 and any other distal diameter reducing ties (if present). However, this is for exemplary purposes only, and the purpose and function of each of the respective first and second rotatable rings 128, 130 can be changed or modified, such that rotation of any particular rotatable knob will facilitate retraction of the particular trigger wires or diameter reducing ties that are attached to the inner surface thereof.

At this point, the stent graft 52 should be fully deployed within the vessel, with the exception of a stent graft that may be fully deployed but the proximal-most stent (such as the bare stent 80 shown in FIG. 8) is still contained within a top cap 300 as shown in FIG. 34. In the case where a top cap 300 is present to contain the proximal stent 80, the user may then grip the rear handle 14 and begin rotating the rear handle. As mentioned previously, rotation of the rear handle 14 causes the second follower 284 to move proximally within the rear rail 282 as the protrusions 302 extending radially outwardly from the second follower 284 engage the threads 296 formed on the inner surface of the rear handle 14. As the second follower 284 moves proximally, it simultaneously causes proximal longitudinal movement of the inner cannula 22 as well as proximal movement of the nose cone 18 and top cap 300. As the nose cone 18 and top cap 300 are pushed proximally, the top cap 300 is lifted off of the proximal stent 80, thus allowing the proximal stent to fully deploy as FIG. 35 shows.

Once the stent graft 52 has been fully released from the delivery device 2, the delivery device 2 can be removed from the patient's body. In one example, it may be desirable to once again cover the nose cone 18, or at least the distal portion of the nose cone 18 and/or the top cap 300 with the sheath 150 before removing the device from the vessel lumen. The distal taper of the nose cone 18 may facilitate efficient and easy withdrawal of the delivery device 2 from the body with reduced risk of the nose cone 18, the top cap 300, or other portions of the delivery device 2 from snagging, catching or otherwise interfering with the deployed stent graft. The delivery device 2 can then be withdrawn distally, through the lumen of the stent graft and retracted further until the device has been safely removed from the patient's body.

Throughout this specification, unless the context requires otherwise, the words "comprise" and "include" and variations such as "comprising" and "including" will be understood to imply the inclusion of an item or group of items, but not the exclusion of any other item or group items. While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A handle assembly for a prosthesis delivery device comprising:

a main handle having an outer surface;

a rotatable handle having a proximal end and a distal end;

a retractable sheath operatively coupled to the rotatable handle;

at least one rotatable ring having a rotatable inner surface, the at least one rotatable ring coupled to a distal end of at least one trigger wire, and the at least one trigger wire having a proximal end configured to releasably engage a prosthesis;

wherein the main handle is fixed relative to the rotatable handle;

wherein the rotatable handle is fixed longitudinally relative to the main handle;

wherein rotation of the rotatable handle retracts the sheath in a distal direction; and wherein rotation of the at least one rotatable ring winds at least a portion of the trigger wire around the main handle in a space between the outer surface and the rotatable inner surface and withdraws the at least one trigger wire in the distal direction.

2. The handle assembly of claim 1, wherein the at least one rotatable ring is fixed longitudinally relative to the main handle and the rotatable handle.

3. The handle assembly of claim 1, wherein the inner surface comprises a groove configured to receive a portion of the at least one trigger wire.

4. The handle assembly of claim 1, wherein the at least one rotatable ring comprises first and second rotatable rings.

5. The handle assembly of claim 4, wherein the at least one rotatable ring comprises first and second rotatable rings and the first rotatable ring is configured to wind at least a portion of the trigger wire onto the inner surface and withdraw the at least one trigger wire in the distal direction and the second rotatable ring is configured to release diameter reducing ties from the prosthesis.

6. The handle assembly of claim 4, wherein the at least one rotatable ring comprises first and second rotatable rings and the first rotatable ring is configured to wind at least a portion of a first trigger wire onto the inner surface of the first rotatable ring and the second rotatable ring is configured to wind at least a portion of a second trigger wire onto the inner surface of the second rotatable ring and withdraw the second trigger wire in the distal direction.

7. The handle assembly of claim 1, wherein the rotatable handle comprises threads on its inner surface.

8. The handle assembly of claim 7, wherein the threads have a constant pitch.

9. The handle assembly of claim 7, further comprising a sheath follower slidably disposed in the rotatable handle and operatively connected to the sheath, wherein distal movement of the sheath follower within the rotatable handle retracts the sheath in the distal direction.

10. The handle assembly of claim 9, wherein the sheath follower comprises protrusions, where the protrusions are having a generally conical, domed or rounded trapezoidal shape.

11. The handle assembly of claim 1, wherein rotation of the at least one rotatable ring positions the trigger wire in contact with the outer surface of the main handle in the space between the outer surface and the rotatable inner surface.

12. The handle assembly of claim 11, wherein rotation of the at least one rotatable ring positions the trigger wire in contact with the rotatable inner surface in the space between the outer surface and the rotatable inner surface.

13. A prosthesis delivery device comprising:

a handle assembly, the handle assembly comprising:

a main handle having an outer surface;

a rotatable handle disposed distally of the main handle;

a retractable sheath operatively coupled to the rotatable handle;

at least one rotatable ring, the at least one rotatable ring coupled to a distal end of at least one trigger wire, the at least one trigger wire having a proximal end releasably engaged with a prosthesis;

a prosthesis retention region;

wherein the prosthesis is releasably coupled to the prosthesis retention region;

wherein the at least one rotatable ring comprises a rotatable inner surface onto which the at least one trigger wire is configured to be wound;

wherein the main handle is fixed relative to the rotatable handle;

wherein the rotatable handle is fixed longitudinally relative to the main handle;

wherein rotation of the rotatable handle retracts the sheath in a distal direction; and wherein rotation of the at least one rotatable ring winds at least a portion of the trigger wire around the main handle in a space between the outer surface and the rotatable inner surface and withdraws the at least one trigger wire in the distal direction.

14. The prosthesis delivery device of claim 13, wherein the at least one rotatable ring is fixed longitudinally relative to the main handle and the rotatable handle.

15. The prothesis delivery device of claim 13, wherein the inner surface comprises a groove configured to receive a portion of the at least one trigger wire.

16. The prosthesis delivery device of claim 13, further comprising a nose cone at a proximal end of the prosthesis delivery device.

17. The prosthesis delivery device of claim 16, further comprising a top cap extending distally from the nose cone and extending over an uncovered proximal stent at the end of the prosthesis.

18. A handle assembly for a prosthesis delivery device comprising:

a main handle having an outer surface;

a rotatable handle having a proximal end and a distal end;

a retractable sheath operatively coupled to the rotatable handle;

a first rotatable ring having a first rotatable inner surface, the at least one rotatable ring operatively coupled to a distal end of a first trigger wire having a proximal end configured to releasably engage a prosthesis;

a second rotatable ring disposed distally of the first rotatable ring and having a second rotatable inner surface, the second rotatable ring operatively coupled to a distal end of a second trigger wire having a proximal end configured to releasably engage the prosthesis;

wherein the main handle is fixed relative to the rotatable handle;

wherein rotation of the rotatable handle retracts the sheath in a distal direction;

wherein rotation of the first rotatable ring winds at least a portion of the first trigger wire around the main handle in a space between the outer surface and the first rotatable inner surface of the first rotatable ring and withdraws the first trigger wire in the distal direction; and wherein rotation of the second rotatable ring winds at least a portion of the second trigger wire around the main handle in a space between the outer surface and the second rotatable inner surface of the second rotatable ring and withdraws the second trigger wire in the distal direction.

19. The handle assembly of claim 18, wherein the first rotatable ring is fixed longitudinally relative to the main handle and the rotatable handle.

20. The handle assembly of claim 19, wherein the second rotatable ring is fixed longitudinally relative to the main handle and the rotatable handle.

21. The handle assembly of claim 20, wherein the first and second inner surfaces each comprises a groove configured to receive a portion of the first and second trigger wires.

* * * * *